United States Patent [19]

Homer et al.

[11] Patent Number: 4,846,081
[45] Date of Patent: Jul. 11, 1989

[54] CALORIMETRY SYSTEM

[75] Inventors: John C. Homer, Chardon; Shahriar Nowshiravani, Mayfield Heights; Steven L. Ross, Cleveland; Gilbert F. Lutz, Chesterland, all of Ohio

[73] Assignee: General Signal Corporation, Stamford, Conn.

[21] Appl. No.: 153,741

[22] Filed: Feb. 8, 1988

Related U.S. Application Data

[63] Continuation-in-part of Ser. No. 36,048, Apr. 8, 1987, Pat. No. 4,809,190.

[51] Int. Cl.$^4$ ............................................. F23H 5/18
[52] U.S. Cl. .................................. 110/186; 110/101 C; 110/101 CF; 110/101 CD; 110/269; 374/36; 414/157
[58] Field of Search .................. 110/347, 269, 101 C, 110/101 CF, 101 CD, 186, 210, 329; 374/31, 34; 414/157

[56] References Cited

U.S. PATENT DOCUMENTS

| | | | |
|---|---|---|---|
| 1,869,585 | 8/1932 | Schmidt | 374/36 |
| 2,026,179 | 12/1935 | Keith | 374/36 |
| 3,988,926 | 11/1976 | Haas | 374/31 |
| 3,994,164 | 11/1976 | Regenass et al. | 374/31 |
| 4,057,396 | 11/1977 | Matovich | 422/202 |
| 4,074,360 | 2/1978 | Stadie et al. | 364/551 |
| 4,108,301 | 8/1978 | Trozzi | 198/633 |
| 4,115,862 | 9/1978 | Stewart | 364/500 |
| 4,126,396 | 11/1978 | Hartmann | 356/434 |
| 4,156,590 | 5/1979 | Pariani | 431/3 |
| 4,324,495 | 4/1982 | Martinez | 198/498 |
| 4,345,463 | 8/1982 | Wilson | 374/36 |
| 4,353,427 | 11/1982 | Stock | 73/1 B |
| 4,386,858 | 6/1983 | Kude | 374/37 |
| 4,438,709 | 3/1984 | Borio et al. | 110/347 X |
| 4,456,389 | 6/1984 | Regenass et al. | 374/31 |
| 4,501,552 | 2/1985 | Wakamiya | 364/477 |
| 4,580,504 | 4/1986 | Beardmore | 110/261 |
| 4,580,698 | 4/1986 | Ladt | 198/505 |
| 4,595,125 | 6/1986 | Alwerud | 198/505 |
| 4,635,572 | 1/1987 | Nickel | 110/343 |
| 4,724,980 | 2/1988 | Farley | 222/55 |

FOREIGN PATENT DOCUMENTS 2111708 9/1972 Fed. Rep. of Germany.

OTHER PUBLICATIONS

Fluid Data Inc., Bull. 20: FC-1, 9/84.

Primary Examiner—Edward G. Favors
Attorney, Agent, or Firm—Martin LuKacher

[57] ABSTRACT

A calorimetry system for measurement of the heating value of coal having a combustor 24 and a mixing unit 30 wherein heat from combustion gases is transferred to air. The system has a gravimetric feeder 64 for providing coal at a measured mass feed rate; the coal including any moisture present therein. The coal is pulverized in an air-driven mill or pulverizer 14 which is fed coal from the feeder and is separated by a cyclone separator 16 into two streams; one carrying coal and air mixed together in a controlled ratio to the combustor. The air which drives the separator, together with fines of the coal and moisture is fed to an afterburner 26 of the combustor so that the thermal dynamics of the entire coal stream is involved in the heating value measurement. Instrumentation measures the flow rates of cooling air, primary air which carries the coal streams into the combustor and secondary combustion air as well as the mass flow rates of the coal into the combustor as measured with the gravimetric feeder. A computer, thermocouples and pressure gauges controls the feeding of the coal and fuel gases (propane) during initiation of combustion, and for computing the heating value of the coal.

30 Claims, 20 Drawing Sheets

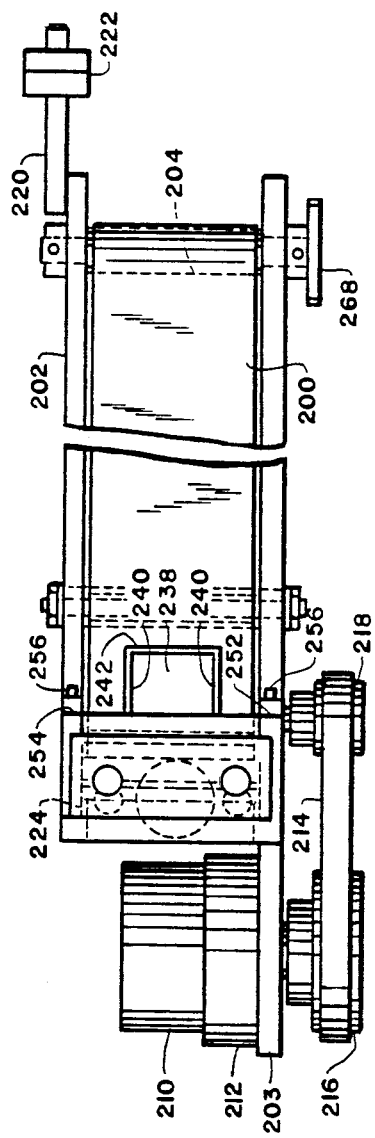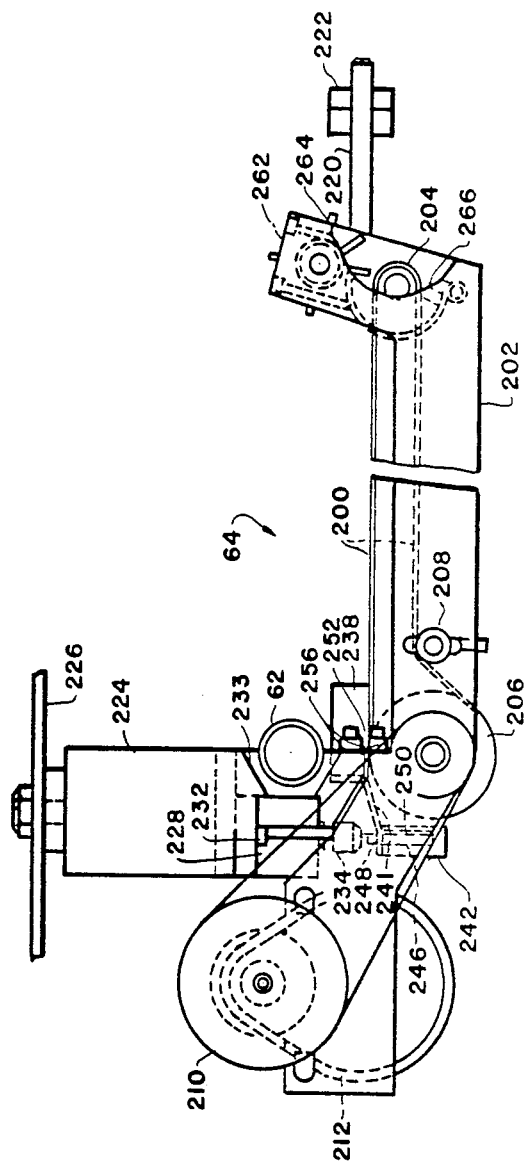
FIG.4
FIG.5

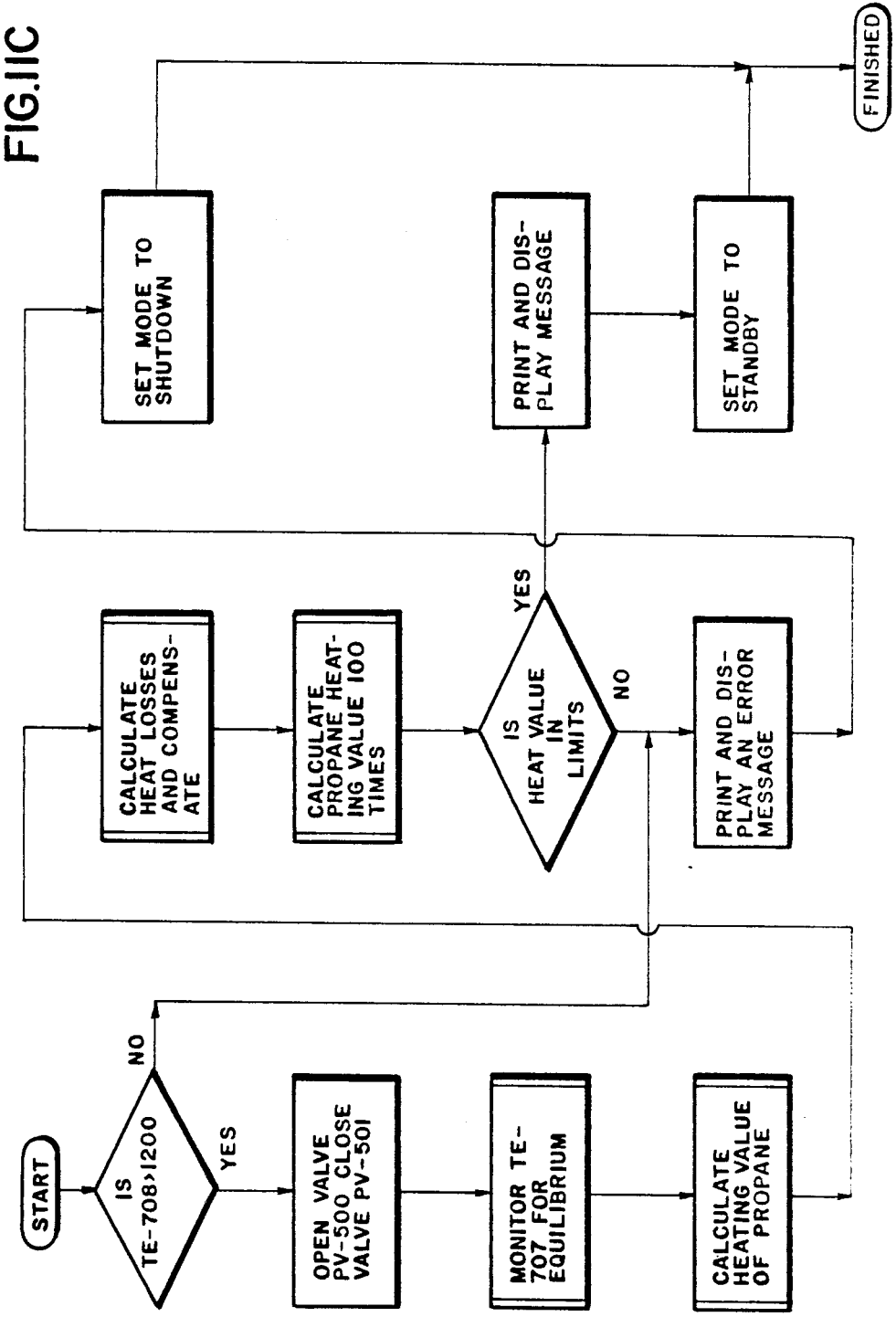

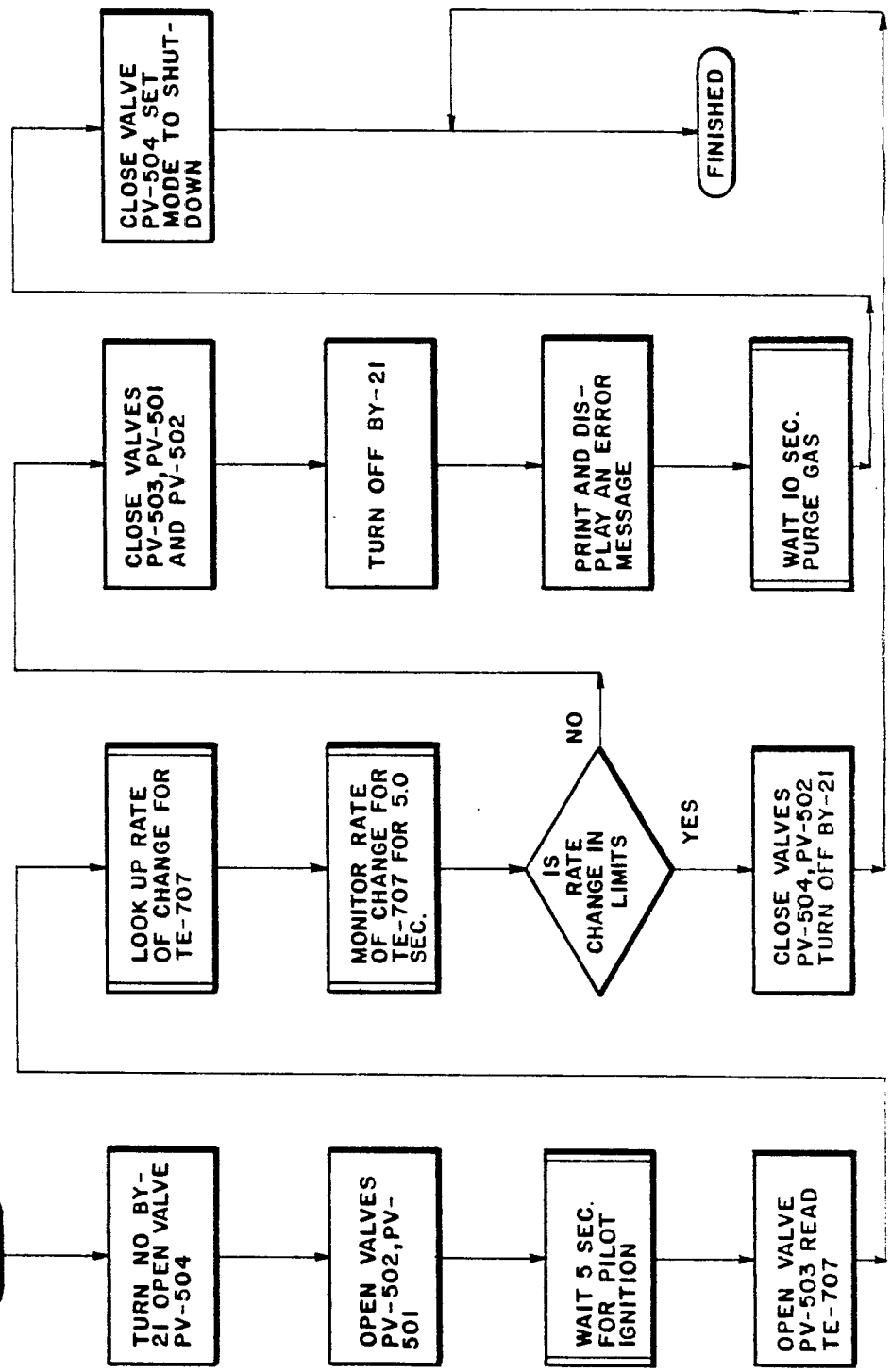
FIG.IIH

CALORIMETRY SYSTEM

The Present invention relates to calorimetry systems, and particularly to a calorimetry system for measuring the heating value or heat of combustion of solid fossil fuels, such as coal, continuously and directly so that the result may be used on line for information as to the heating value of the coal, and if desired its sulfur and ash content.

This application is a continuation in part of U.S. Pat. application Ser. No. 036,048 filed Apr. 8, 1987 Pat. No. 4,809,190 in the names of John C. Homer, et al., which describes a calorimetry system with respect to which the system provided by this application is an improvement. Features of this application provide improvements in the accuracy of measurement of the heating value, enable the system to be used to measure the heating value of moist coal, and allow for the simultaneous measurement of heating value with the measurement of the sulfur content and of the ash content of the coal.

Included as an appendix to this application is the aforesaid patent application by Homer et al., which describes a calorimetry system for measuring the heats of combustion (heating value) of solid fuels such as coal by the continuous combustion thereof, rather than, as in the past, by combustion of a discrete sample of the coal as with a bomb calorimeter. Techniques of measuring heating value on a continuous basis heretofore required reliance on indirect chemical and physical analysis, such as with X-ray fluorescence or neutron bombardment (the so-called prompt neutron activation analysis technique). Continuous flow combustion calorimetry has been used to measure the heat of combustion of gaseous fuel; however the accurate continuous combustion calorimetry of solid fuels, particularly coal, has not been obtained prior to the invention described in the aforementioned patent application.

This invention has as its principal feature improving the accuracy of measurement of the continuous flow calorimetry system described in the above identified application and to enable measurements to be made with moist coal of low heating value as is commonly used by public utilities in the United States.

Another feature provided by the present invention is to provide an improved gravimetric belt feeder capable of measuring the mass feed rate of solid fuel, particularly coal, to a high degree of accuracy (for example, less than 2% measurement error).

A still further feature of the invention is to provide an improved combustor for coal calorimetry wherein more reliable ignition is facilitated by a remote mounted (from the coal combustion chamber) ignition device which is immune to the high temperature effects of the combustor. There is a high degree of assurance that all parts of the coal stream are burnt by using an afterburner which receives fines, together with moisture from the coal and air. The air drives a separator for producing coal particulates from which a controlled mixture of coal and air can be obtained for combustion. The combustor also has improved means for clean out of channels through which the mixture of coal and air is supplied thereto.

Another feature of this invention is to provide an improved calorimetry system for obtaining the heating value of solid fuels, particularly coal, as well as its sulfur content and also its ash content wherein heating value, sulfur and ash content can be measured simultaneously and the measurements can be made in real time.

Briefly described, an improved calorimetry system in accordance with the invention has a feeder which measures the mass feed rate of coal or other solid fuel including the moisture thereon or therein. For optimum combustion of the coal, a controlled ratio of air and coal is obtained by pulverizing or milling the measured mass of coal, which arrives continuously from the feeder, and separating the coal into first and second streams, one of which contains substantially all of the coal which has been milled to predetermined size and which is mixed with primary air in a controlled coal to air ratio. The other stream from the separator may contain coal fines and moisture. The exclusion of this second stream from the calorimeter would introduce a measurement error of the heating value of the coal. The primary coal and air stream, because of its controlled mixture, is combusted entirely in the combustor with secondary air which passes through a permeable enclosure which serves to minimize heat loss from the combustor to the ambient by way of radiative losses through the walls of the combustor. The second stream of air, fine coal and moisture is introduced into an afterburner wherein all of the coal is exposed to the exhaust flame from the combustor so that it may be burned and contribute to the heating value measurement without contaminating the secondary air which is supplied through the permeable enclosure to the combustor.

In order to initiate combustion and bring the system to a temperature which will support spontaneous combustion of the mixture of coal and air, a gaseous fuel, preferably propane, is used. This fuel can be used in an igniter which introduces a flame into the combustor so as to ignite the fuel gas which is initially introduced therein to preheat the system to a temperature which enables the spontaneous combustion of the coal and also to calibrate the system. Preferably the propane use for calibration purposes is substantially pure propane.

The combustion gases are mixed with cooling air and the heating value is determined by a method of mixtures technique. Instrumentation is provided for measurement of temperatures and mass flow rates of the air and air/fuel mixtures which enter the combustor, and also of the cooling air which is used for mixing, so that the enthalpy of all of the constituents which affect parameters of the heating value computation is taken into account in the heating value computation. A computer is preferably used to respond to the measurements from the instrumentation and provide the heating value computations which may be printed out and/or displayed. The measurements may be used in real time to control processes using the coal, such as the rate at which coal is fed to a boiler in a public utility or to check the quality of the coal going into storage in a facility, such as the coal storage yard of a public utility.

The combustion gases from the calorimeter may be supplied to a sulfur dioxide measurement device for the continuous on-line measurement of the sulfur content of the coal stream. The flue gases may also be passed through a device which collects the ash, wherein the ash is weighed, so as to measure the ash content of the coal. The combustor converts substantially all of the fuel into combustion gases without deposition of any ash in the combustor. Accordingly the ash measurement device provides accurate ash content measurements from the combustion gases.

The gravimetric feeder is capable of more accurate measurements of the mass feed rate of the coal than was the feeder described in the above mentioned United States patent application by means for controlling of the length of a body of coal. The body of coal is disposed on a lever defined by a moving belt onto which the coal is deposited, and which moves continuously between a tail and a head end pulley. Means are provided in cooperative relationship with the belt as it rotates around the head end pulley for providing a defined angle of repose of the end of the body of coal which is deposited on the belt and which is fed from the belt into the mill and separator of the calorimetry system. Such means is preferably provided by utilizing a rotating member which engages the coal adjacent to the head end pulley at a velocity at least slightly in excess of the velocity of the belt as it travels around the head end pulley. The coal does not therefore back up on the belt. The head end pulley is of minimum diameter to enable the belt to conform to it and remain in engagement with its periphery. The tendency is minimized of the coal to adhere to the pulley and thereby to effectively increase the length of the lever arm by indeterminate amounts, which can depend upon its cohesivity which is a function of several variables, including ambient, environmental conditions. The pivotal support for the feeder, which defines the fulcrum of the lever, and a force measurement device (e.g., a load cell) are preferably made of material having substantially the same coefficient of thermal expansion so that the lever arm lengths and the forces which are measured by the load cell do not contain errors due to differential thermal expansion.

The foregoing and other objects features and advantages of the invention as well as a presently preferred embodiment thereof, and the best mode now known for practicing the invention, will become more apparent from a reading of the following description in connection with the accompanying drawings in which:

FIG. 4 is a top view of the gravimetric belt, feeder shown in FIG. 2 with the overhead support 226 removed;

FIG. 5 is an elevational view of the feeder shown in FIG. 4;

Figure 1:
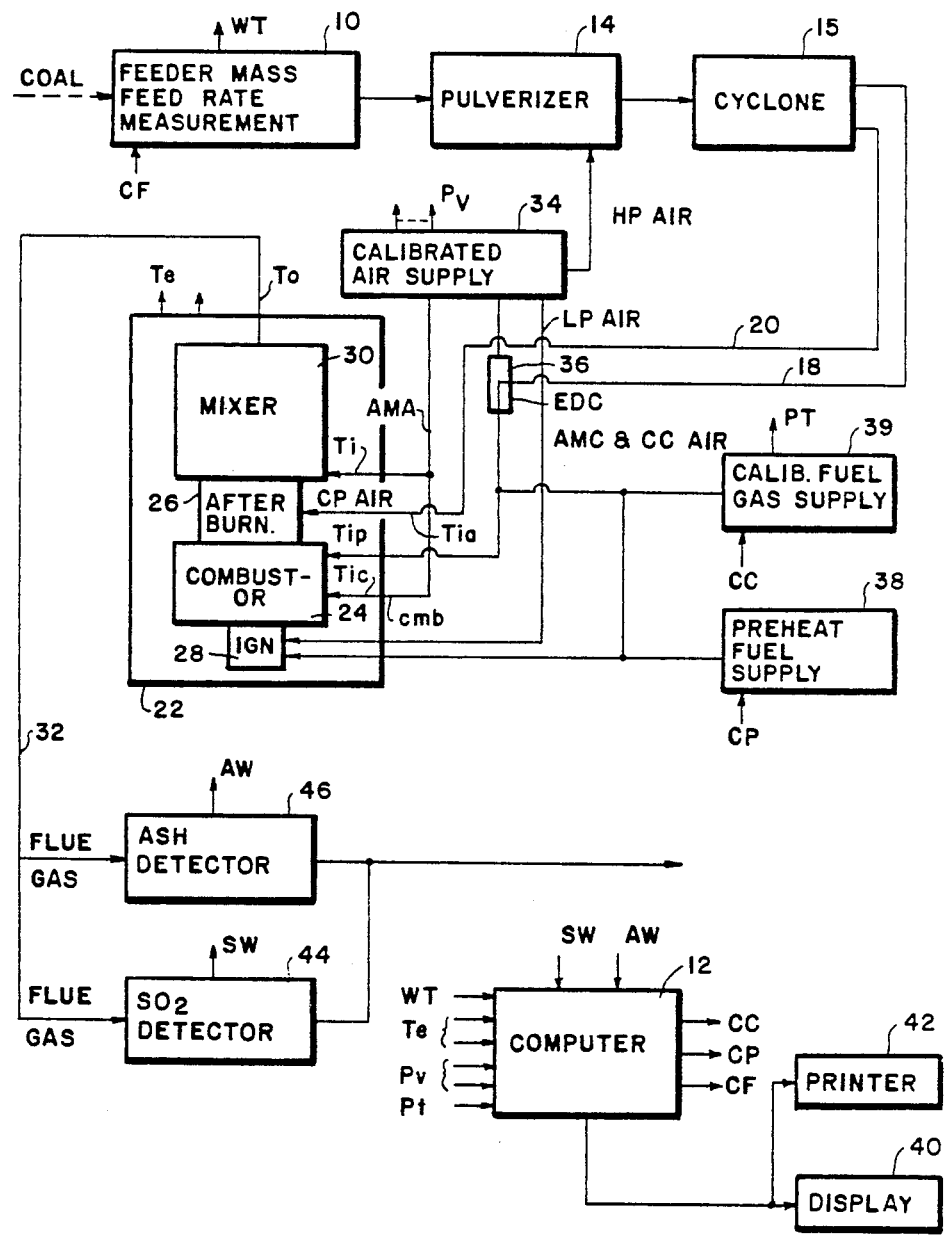
FIG. 1 is a simplified block diagram of the improved calorimetry system provided in accordance with the invention.
Figure 3:
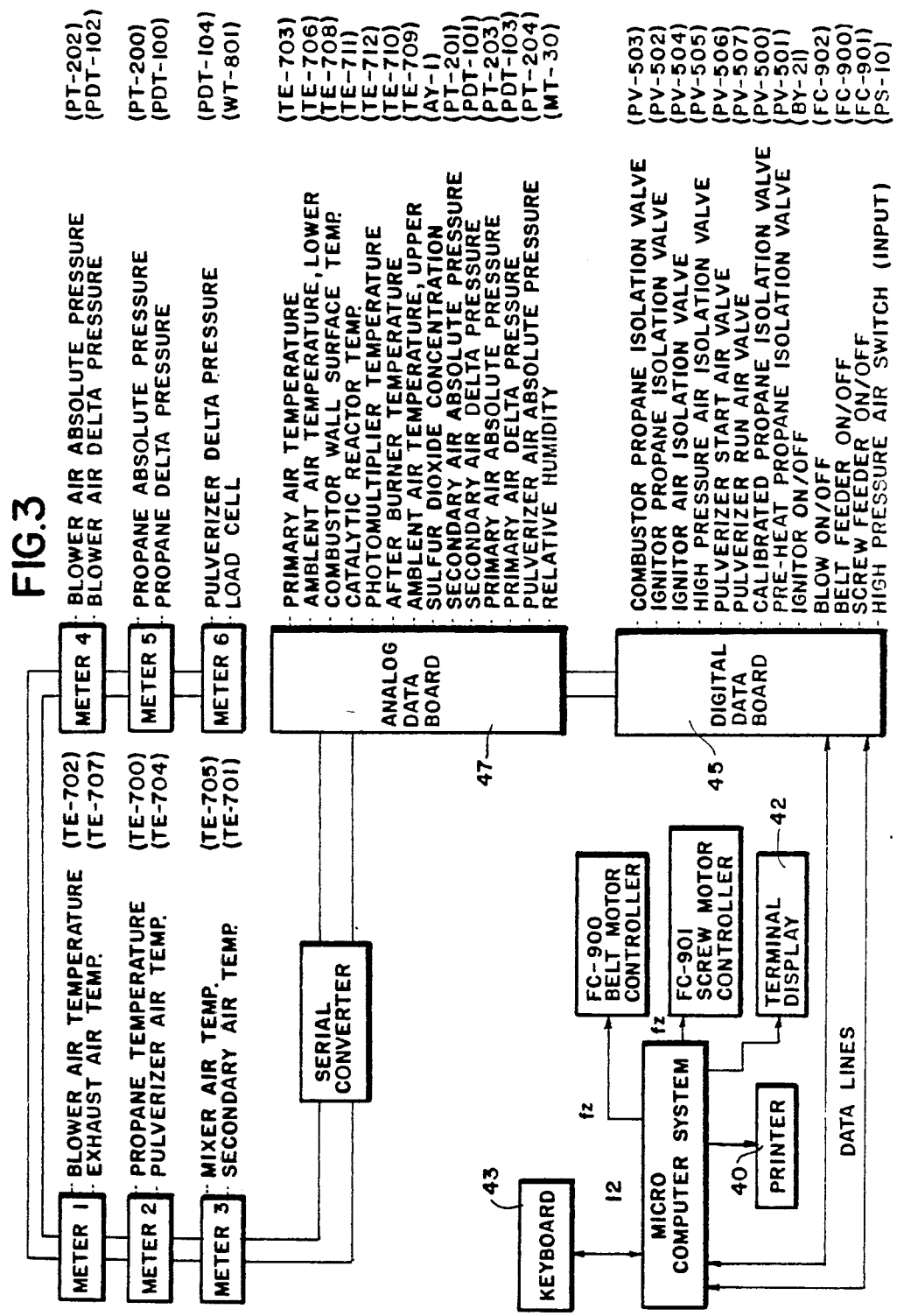
FIG. 3 is a block diagram of the electronic computer control and measurement system which is used in the calorimetry system shown in FIGS. 1 and 2.

FIGS. 11A through J are flow charts illustrating the format and structure of the program utilized in the computer shown in FIGS. 1 and 3.

Referring more particularly to FIG. 1 there is shown an input coal supply to a feeder 10 which provides a mass feed rate measurement. The output of the feeder is a force measurement indicated as WT which is converted into a mass feed rate measurement by taking into account the feed rate of the coal along a lever arm provided by a belt which extends between tail and head end pulleys. This feeder is shown in greater detail in FIGS. 4 through 7, and will be described fully hereinafter. The computer 12 provides a control output CF to the feeder which controls the speed thereof so as to maintain the feed rate essentially constant. The feeder is designed in accordance with features of the invention to provide for high accuracy of measurement by assuring that the length of the lever arm, which produces a reaction force measured by a load cell to provide the WT output, is constant during operation of the feeder.

The coal is delivered from the feeder to a pulverizer 14. The pulverizer is a fluid energy mill in that it is driven by high pressure air (HP air) which is the source of pulverizing energy. The coal from the feeder is, for example, approximately 30 mesh. The pulverizer 14 reduces the coal to micron size. The moisture in the coal remains during the feeding and the pulverizing process.

The coal for combustion is desirably separated from the air which energizes the pulverizer. Practical separators, such as the cyclone 16, which is used to separate the coal from the air, entrains with the air a small quantity of ultrafine coal, for example, approximately 1% or less of the pulverized coal. In order to provide high accuracy in the heating value measurement, this coal must also be accounted for. The moisture is also carried by the air and must be accounted for. To this end two streams are obtained from the cyclone 16; an essentially solids discharge stream along the line 18 and an essentially gaseous discharge stream along the line 20. Both of these streams are supplied to the calorimeter 22.

The calorimeter includes a combustor 24 which has an afterburner 26. Ignition of the gases in the combustor is started by an igniter 28. The calorimeter also includes a mixer 30 which mixes the combustion gases with cooling air. The air and the combustion gases leave the mixer as flue gas along the line 32. The temperature rise of the combined combustion gases and cooling air is used together with the mass feed rates of the coal and the total air entering the calorimeter 22 to compute the heating value of the coal. These temperature measurements are obtained from thermocouples and other temperature measurement devices and data representing them are applied to the computer 12 together with pressure measurements PV which are obtained from flow measurement devices in lines of a calibrated air supply 34. In practice, the supply 34 is provided by a blower and an oil free 100 psi source, and will be discussed more fully in connection with FIG. 2.

The temperature and pressure of the air determines the density of the air which affects the mass flow rate of the air (viz, the enthalpy of the system). The air which energizes the pulverizer and carries a controlled mixture of air and coal particles of the cyclone 16 is obtained from the calibrated air supply 34. The pressure measurements PV which determine the flow are shown for simplicity as being taken from the calibrated air supply. The temperature measurements shown at Te are taken in the lines directly leading into the calorimeter as will be more fully shown in, and explained in connection with, FIG. 2. The coal particles from the cyclone 16 are educed with low pressure air (LP air) from the supply 34 by means of a Venturi educer 36. The air containing the moisture and ultrafine particles is supplied to the afterburner 26 where the ultrafine coal is combusted in the flame from the combustor.

To start ignition in the combustor, a preheat fuel supply 38 of fuel gas, such as propane, is supplied to the igniter together with air from the air supply 34. The igniter includes an electrically operated spark source which is energized upon command from the computer and de-energized when combustion is detected as by a rise in the temperature of the flue gas in the line 32. The preheat gas (which can be ordinary commercial grade Propane) is also supplied to the combustor during a preheat cycle.

When the combustor 24 is preheated to a temperature of between 1500° F. and 1700° F. as measured by a thermocouple which measures the temperature of the combustor, a calibration mode is entered wherein essentially pure fuel gas (propane having a heating value which is known to a high degree of accuracy) is supplied to the combustor. This calibration mode is carried on without the introduction of any coal from the feeder, pulverizer and cyclone.

After calibration a standby mode is entered while the temperature of the calorimeter is maintained with the gaseous fuel from the preheat fuel supply. In order to analyze coal, an analyze mode is entered. The feeder 10 is brought up to speed. The weight is monitored so as to obtain data that coal is being fed from the feeder into the pulverizer. Now both propane from the supply 38 and coal are entering the combustor 24. The temperature of the combustor and the flue gas increase indicating that coal combustion is taking place. The propane supply 38 is terminated and coal combustion continues. The measurements of temperature and pressure are supplied to the computer and the heating value of the coal is continuously determined in real time. These values can be displayed and printed with the display updated and printing occurring at fixed intervals, such as 1 minute, 5 minutes ½ hour, etc. The computer may also average the heating value measurements during each interval.

The flue gases may also be analyzed, continuously and in real time, for sulfur and ash content. FIG. 1 illustrates a sulfur dioxide ($SO_2$) detector 44 and an ash detector 46 in the flue gas stream. The $SO_2$ detector may divert a sample of the flue gas to an analyzer, such as an ultraviolet spectrometer of the type which is commercially available. The $SO_2$ output SW is supplied to the computer which may control the display and print out so as to provide readings averaged over the readout intervals. The ash detector 46 may be a electrostatic precipitator which has vibrating plates. The ash precipitates on the plates and is continuously weighed to provide an analog weight output signal AW which is digitized (as was the $SO_2$ signal) and supplied to the computer for computation of the statistics of the measurements of the ash and sulfur content. These ash and sulfur signals may be used together with the heating value data to control the mixture of the coal with other coals which have previously been measured to provide coal of predetermined sulfur content. The ash detector is enabled to provide accurate measurements of ash content since the combustor in the calorimeter 22 collects essentially no ash but rather causes the entrainment of all of the ash with the combustion gases so that they pass out of the calorimeter 22 completely with the flue gas. Parallel operating with the $SO_2$ analyzer is possible because of the very small quantity of total flue gas required for $SO_2$ analysis.

Equations (1), (2) and (3) given below are used to compute the heating value of the coal in the computer 12.

$$C_p \text{delta} T = kk[aa(T_o - T_i) + bb(T_o^2 - T_i^2)/2 + \quad (1)$$

$$cc(T_o^3 - T_i^3)/3 + dd(T_o^4 - T_i^4)/4]$$

$$Q = (ama + amc + ccair + cpair) C_p \text{delta} T + \quad (2)$$
$$C_{pair} [cmb(T_i - T_{ic}) + ccair(T_i - T_{ip}) +$$

$$cpair(T_i - T_{ia})]$$

$$hv = Q/amc + 410[f(\text{delta } T_{amb})]/amc \quad (3)$$

where, aa, bb, cc, dd, kk: are coefficients—which are the same for each rank of coal (e.g., bituminous, subbituminous, lignite, etc.), $T_o$, $T_i$ are heat exchanger outlet and inlet temperatures; ama is heat exchanger air mass flow rate plus combustion air cmb; amc is coal mass flow rate; ccair is primary air mass flow rate; cpair is pulverizer air mass flow rate; $T_{ic}$ is combustion inlet air temperature; $T_{ip}$ is primary air inlet temperature; $T_{ia}$ is afterburner air temperature; hv equals coal heating value BTU/pound; and cmb is the combustion air mass flow rate.

Figure 2A:
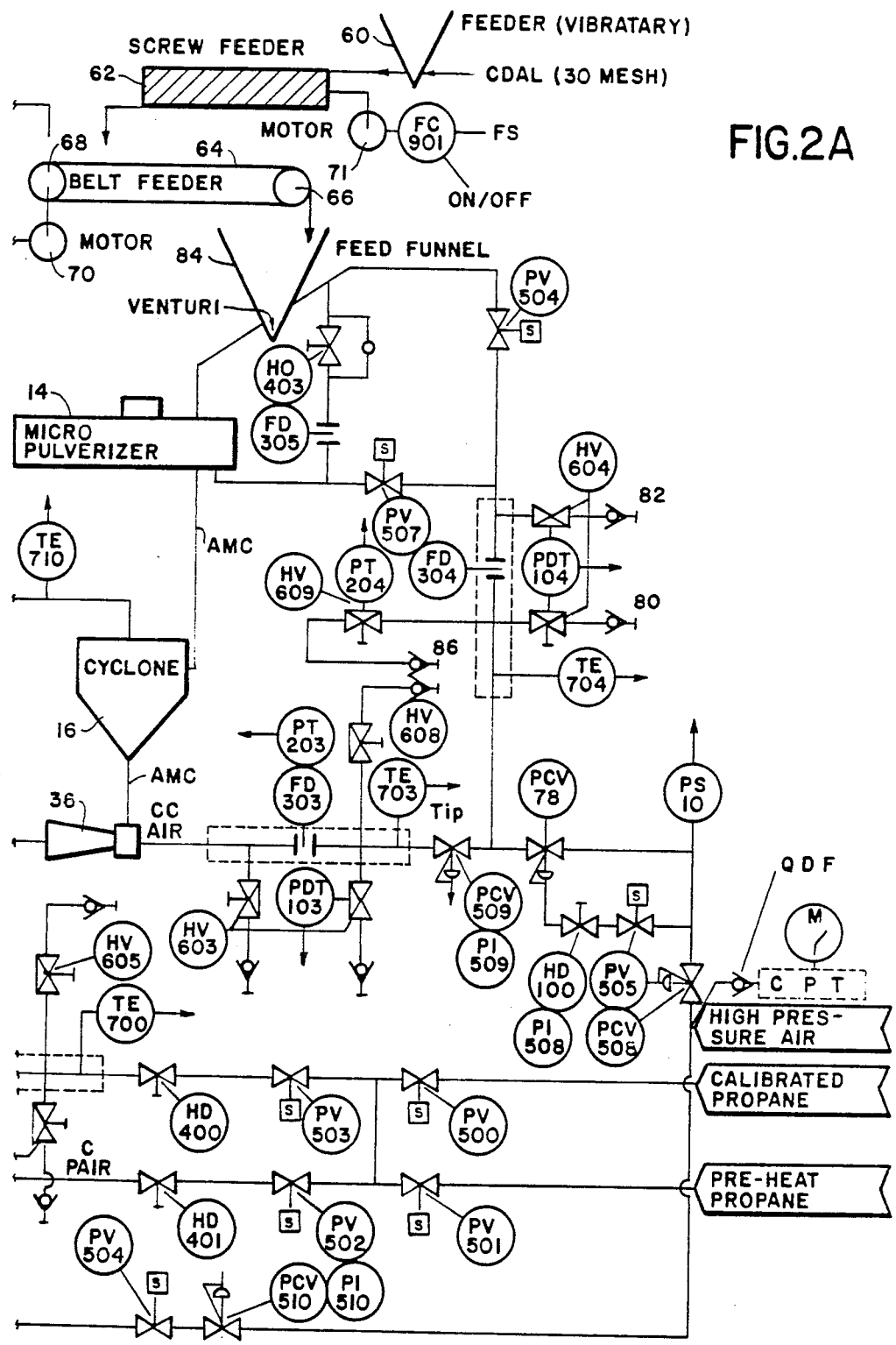
FIG. 2 is a schematic diagram illustrating the improved calorimetry system and showing the plumbing and instrumentation thereof in greater detail.
Figure 2B:
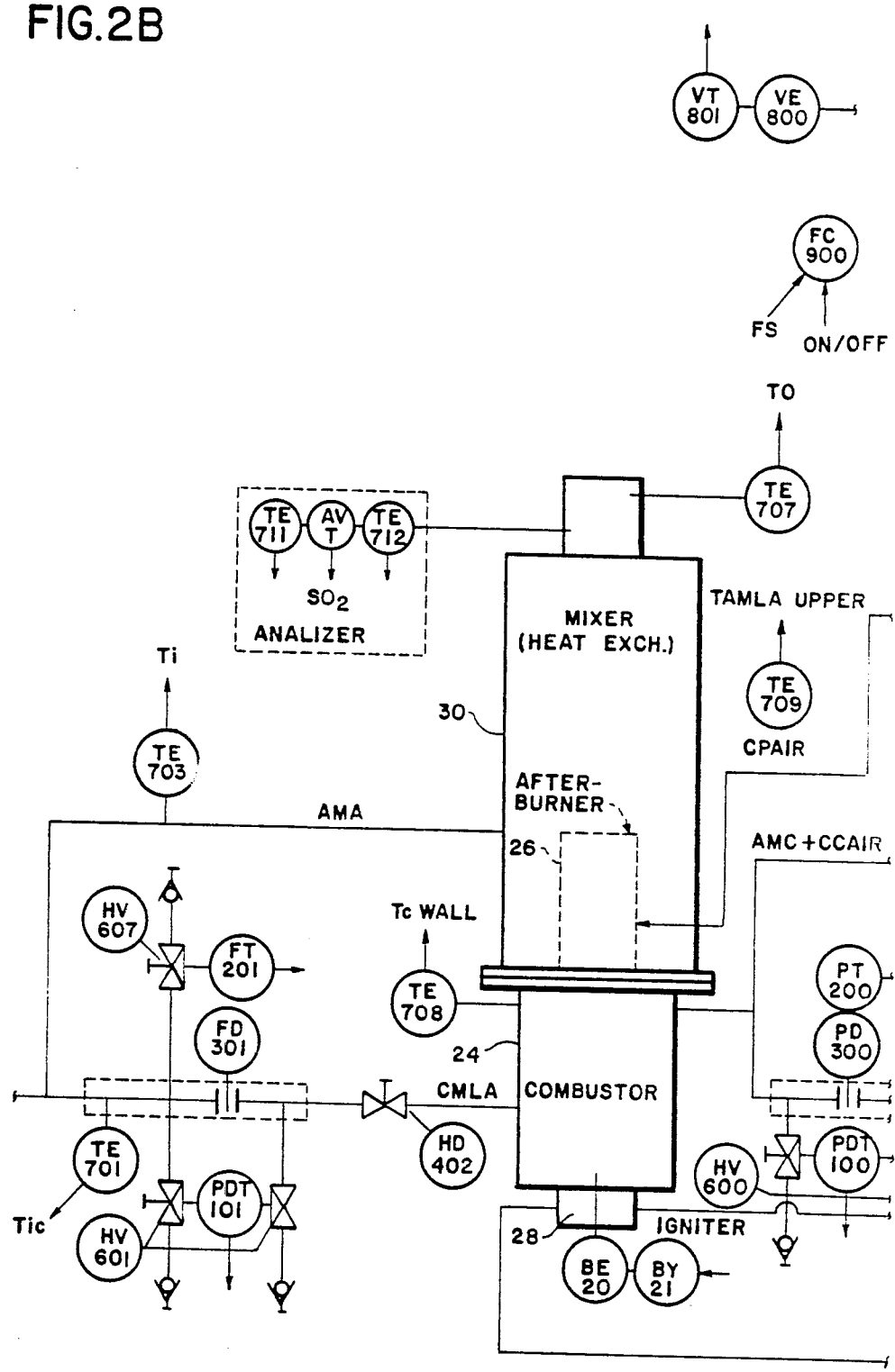
Figure 2C:
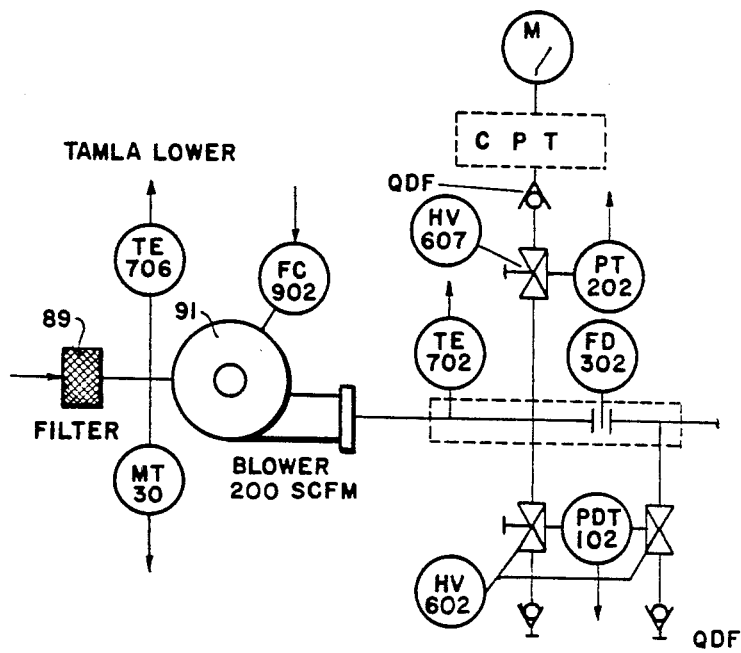

These designations are shown in FIGS. 1 and 2 at the lines carrying the respective air flows and where the respective temperatures are measured.

In equation (3), the term $410[f(\text{delta } T_{a\,m\,b})]/amc$ is the nonspecific heat loss which is determined empirically based upon the differences between the heating value measured with the calibrated propane and the known heating value of the calibrated propane. The term includes a factor $f(\text{delta} T_{a\,m\,b})$ which is a function of the difference between the ambient temperatures $T_{amb}$ upper and $T_{a\,m\,b}$ lower as measured by a thermocouple outside of the calorimeter (near the wall of the mixer and combustor) and the temperature of the mixing air $T_i$ (also referred to as cooling air above) as shown in FIG. 2. These temperatures are used because the nonspecific heat loss is a function of the ambient temperature. The coefficients aa, bb, cc, dd, and kk may be determined in a manner similar to that discussed in the above referenced U.S. Pat. application Ser. No. 036,048. These values are also obtainable from texts on the thermodynamics of coal. Reference may be had to Chemical Engineers Handbook fifth edition, published by the McGraw Hill Book Company, Copyright 1973 in the section on heat capacity which will be found on pages 3-235 through 3-238, or appendix A entitled Property Data Bank in the text, The Properties of Gases and Liquids, by Reid et al. (McGraw Hill, N.Y. (1977)). These coefficients are equivalent to the WXYZ coefficients of the equation identified by (4) in the above referenced patent application where the derivation of these coefficients is shown.

Referring more particularly to FIG. 2, the thirty mesh coal, which may be sampled from the coal stream to the boiler for real time control of the coal feed to the boiler in accordance with the heating value thereof, is fed into a vibratory feeder 60. From the feeder 60 the coal enters a screw or auger type feeder 62 from which it is deposited onto the belt of the gravimetric, belt feeder 64. Feeder 10 (FIG. 1) is a combination of the screw and belt feeders. The belt feeder is shown diagrammatically in FIG. 2 as having a head end pulley 66 and a tail end pulley 68 which is driven by a stepping motor 70. The stepping motor is controlled by a motor controller indicated as FC900 to which on-off control signals and speed control signals $f_s$ from the computer are fed (see also FIG. 3). The frequency of the $f_s$ signals (which may be pulses) determines the speed of the motor when it is turned on or off by the on-off control signals from the computer via a digital data board 45 (FIG. 3) which contains buffers and drive amplifiers. The $f_s$ signals are provided directly from the computer 12 (FIG. 3). The control signals to a similar motor 71 which drives the screw feeder 66 are also provided from the computer 12 and digital data board 45 to the FC-901 controller.

The feeder defines a lever which is supported on a fulcrum as will be more fully explained in connection with FIGS. 4 through 8. The reaction force corresponding to the weight of the coal on the belt is measured by a load cell, indicated at WE800. The transducer amplifier of the load cell, indicated at WT801, provides an analog signal corresponding to the force developed due to the weight of the coal on the belt. This analog signal is provided to one of six metering circuits and a serial converter which is connected to an analog data board 47 of the electronic portion of the system, shown in FIG. 3 and which will be described hereinafter.

The mass feed rate of the coal is determined from the force measurement, the speed of the motor 70 and other parameters which will be explained hereinafter in connection with FIGS. 4 to 8. As will be described in connection with FIGS. 4 to 8 a strip of coal of constant thickness ad length is measured, since the end of the strip at the head end pulley 66 is controlled by controlling its angle of repose on the pulley. The measurement is used in determining the heating value of the coal in accordance with the equations (1) to (3) given above.

In order to provide micron size coal to the calorimeter 22 so that it will be spontaneously combustible and burn completely with essentially no collection of ash in the combustor 24 of the calorimeter 22, the coal is pulverized by the fluid (air) energy driven micropulverizer 14. The air for driving the pulverizer (supplying the fluid energy for pulverization) is high pressure air from a compressor which supplies the air at, for example, 100 to 150 PSI. The air supply may be calibrated using calibrated pressure transducers and meters which are connected during calibration to quick disconnect one way fitting; thus providing the calibrated air supply 34 (FIG. 1). Two of these transducers (CPT) attached to the fittings (QDF) and their meters (M) are shown in dash lines at the high and low pressure air inputs provided at the high pressure air 100-150 PSI line and the blower 91. The air is regulated by a pressure control valve PCV508 with an indicator PI508 as shown symbolically in FIG. 2. This valve is also known as a regulator valve. It may suitably be set at 100 PSI.

The presence of an underpressure condition is indicated by a pressure switch PS10, which provides an output to the computer 12 for shutting down the system in the event of an underpressure condition. The regulated pressure is provided by a pilot operated regulator valve PCV78. The pilot pressure is obtained by a solenoid operated valve PV505 and a two-way hand operated valve H0100. To start the flow of high pressure air for carrying the coal to the micropulverizer 14, the solenoid of PV505 is operated with a control signal from the computer. This provides pilot pressure to open the pilot operated regulator valve PCV78. The temperature of the high Pressure air is measured by TE704. Temperature measuring devices may be a thermocouple or a Resistance Temperature Detector (hereinafter RTD). The flow of this air is measured by a differential pressure transducer PDT104 which is connected through a pair of hand operated 3-way valves HV604 across an orifice plate FO304. These valves permit connection to remote instruments via 80, 82 and 86 to permit maintenance and calibration of PDT104 and PT204.

High pressure air of known temperature and flow rate (enthalpy) is allowed to enter a Venturi feed funnel 84. Valves PV506 and PV507 are operated in sequence by the computer, and together with H0403 and FO305 start and maintain pulverizer operation. Air flow through the Venturi develops a negative pressure in the feed funnel for drawing the coal therein to the micropulverizer, wherein multiple collisions of the particles, caused by air jets, fracture the coal to a size small enough to ensure complete combustion during its brief residence in the calorimeter combustion chamber.

The air carries the pulverized coal from the micropulverizer (the air driven mass of coal, amc) to the cyclone separator 16 which separates the coal into the primary stream of pulverized coal (amc) and a second stream consisting of the air which circulates around the cyclone, the moisture in the coal and the small percentage of ultrafine coal which is separated with the air from the micron size coal remain in the stream cpair delivered by the cyclone. It is this separated air (cpair) which is supplied to the afterburner 26 of the combustor 24 of the calorimeter 22, as was explained in connection with FIG. 1.

Returning to the high pressure air, the absolute pressure of that air may be measured by a pressure transducer PT204 to supply an absolute pressure signal to the computer. The hand operated valve HV609, which may be connected to a calibration gauge through the quick disconnect fitting attached to HV609, is used to divert the high pressure air to the pressure transducer PT204 for absolute pressure measurement. A similar valve HV608 and pressure transducer PT203 may be used for absolute pressure measurement of the air (the ccair) which carries the pulverized micron size coal separated in the cyclone 16 to the combustor 24 of the calorimeter 22.

The pressure of the carrier air (ccair) is controlled, suitably reduced to 10 PSI, by an instrumented pressure control or regulator valve PCV509, PI509. The temperature and mass flow rate of the carrier air is obtained by an assembly of a thermocouple TE703, an orifice plate F0303 and differential pressure transducer PDT103 which is connected across the orifice F0303 by hand valves HV603. Thus, the mass flow rate of the air and mass flow rate of the coal (amc+ccair) supplied to the combustor is continuously monitored and measured. The temperature of the air fed to the afterburner (the cpair) is measured by TE710 which provides the temperature signal $T_{i\,a}$ which was discussed in connection with FIG. 1. The ambient temperature in the vicinity of the mixer or heat exchanger 30 of the calorimeter 22 is measured by TE709 which provides an output corresponding to $T_{a\,m\,b}$ upper from which the coefficient for controlling the offset due to heat losses from the calorimeter can be obtained and used in the heating value computation (see equation (3) above).

The secondary, low pressure mixing air is drawn through a filter 89. The temperature of this air is measured by TE706 and its relative humidity is also measured by a relative humidity detector MT30. The output of TE706 is indicated as $T_{a\,m\,b}$ lower and is used with $T_{a\,m\,b}$ upper to determine the heat loss if any from the combustor portion of the calorimeter 22 (see equation (3)).

A blower 91 provides the total low pressure air. The blower is turned on and off by controlling power to its motor via a motor control FC902 which receives control signals from the computer via the digital data board 45 (FIG. 3). The temperature of the low pressure air from the blower is monitored by TE702. The absolute pressure of the low pressure air and its flow rate is determined by an assembly consisting of hand valves HV602 and HV607, pressure transducer PT202, the calibration of which can be checked by a calibrated pressure transducer CPT and gauge which may be connected to the quick disconnect fitting QDF. The differential pressure is measured by PDT102 across the orifice plate FO302. The low pressure mixing air has its temperature measured at a point closer to the mixer 30 of the calorimeter 22 by TE705 to assure that the temperature drops in the lines to the input of the mixer 30 are accommodated. The mixing or cooling air which mixes with the combustion gases is therefore supplied together with measurements of its temperature, pressure and flow rate so that the mass flow rate of this air may be computed in the computer 12. In other words, secondary air to the combustor is measured at FO301. FO302 measures total blower air output, which later splits into secondary (combustion) air and tertiary (mixer) air. The proportions are adjusted by HO402. Primary air (High Pressure Air from the oil free compressor), designated ccair, is measured at FO303.

The combustion or secondary air cmb is supplied through a hand valve HO402. The temperature, absolute Pressure and flow rate of the combustion air is measured by a similar assembly as used for measuring these parameters of the other air components to the calorimeter, namely TE701, a pressure transducer PT201 and a pressure transducer PDT101, hand valves HV601 and HV606 apply the pressure to these transducers PT201 and PDT101. There are also quick disconnect fittings for connection of calibrated pressure transducers.

In order to initiate combustion and perform preheating and also to calibrate the calorimeter, two sources of fuel gas, namely preheat fuel gas (propane) to initiate combustion and preheat the calorimeter and a source of substantially pure propane of measured heating value (calibrated propane) are provided. The preheat propane is supplied through two solenoid control valves PV501 and PV503 and an assembly of TE700 and absolute pressure transducer PT200 and valve HV605 and a flow-rate differential pressure measurement device consisting of an orifice plate FO300, two coupled hand valves HV600 and a differential pressure transducer PDT100, all of which can be calibrated using an accurate pressure transducer and meter through quick disconnect fittings.

Figure 10A:
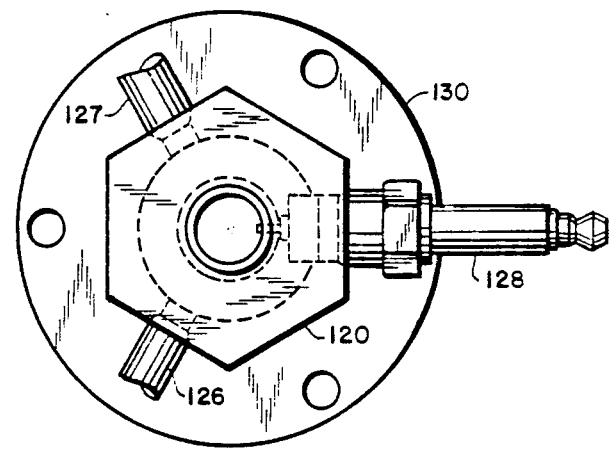
FIG. 10A is a bottom view of the igniter shown in FIG. 10.
Figure 10B:
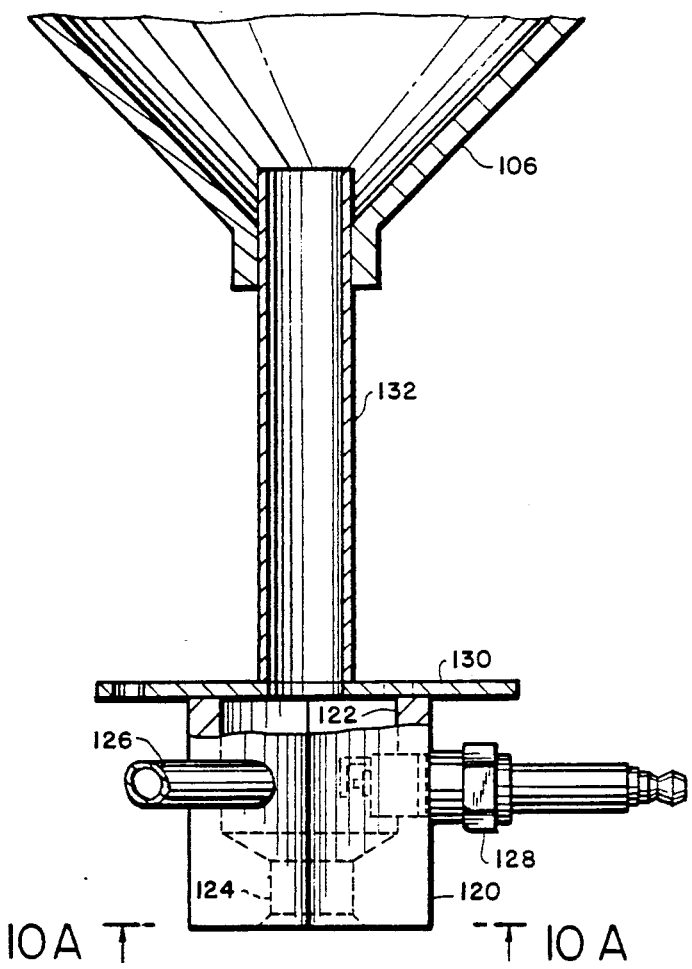
FIG. 10 is an enlarged, fragmentary, sectional view showing the igniter which is disposed at the bottom of the combustor as shown in FIG. 8.

This propane is also shunted through another solenoid control valve PV502 and a hand-operated valve OH0401 to the igniter 28 below the combustor 24. Air to the igniter is supplied from the high pressure air source through an instrumented pressure control regulator valve PCV510, PI510 and a solenoid control valve PV504. A control pulse generated in response to a computer signal is applied to a primary of a transformer BY21 or spark coil to provide a high voltage pulse to a spark plug BE20 in the igniter. On start up of the system, air and preheat propane are provided to the igniter while preheat propane is provided to the combustor 24 and the igniter is pulsed to ignite a flame in the igniter which ignites the preheat propane in the combustor. The igniter 28 is shown in, and will be described more fully hereinafter in connection with, FIGS. 8, 10 and 10A.

The igniter is shut off after ignition by closing the valves PV502 and PV504. Preheat propane continues to be supplied through the solenoid valves PV501 and PV503 and the hand-operated valve HO400. The temperature, flow rate and pressure of this preheat propane is measured with TE700, the pressure transducer PT200 and the differential pressure transducer PDT100. Preheat propane is continually supplied until the temperature of the combustion chamber wall, $T_c$ wall, as measured by TE708 reaches operating temperature (which will support ignition of the coal in the combustor). The wall temperature of the combustor $T_c$ wall is measured by the thermocouple TE708.

When operating temperature is achieved, the calibrated propane is supplied through the valves PV500 and PV503; the preheat propane supply valves PV501 and PV502 being closed by deactuation of their solenoids. The mass flow rate pressure and temperature of the calibrated propane is monitored by PT200, TE700 and PDT100 and the heating value of the calibrated propane is measured and compared with its known heating value so that offsets in the heating value computation can be obtained.

The system is then placed in standby mode with the calibrated propane supply cut off and the preheat propane resupplied to the combustor. When coal is to be analyzed, the screw feeder motor 71 is turned on at high speed, as is the belt feeder motor 70. The coal is supplied (amc+ccair) with the primary air from the high pressure air source. When operating temperature is achieved, the preheat propane is turned off and the heating value of the coal is analyzed using the temperature measurements of the input mixing air ($T_i$) from TE705 and the output temperature of the combustion gases $T_o$ from TE707. The computer determines the mass feed rates of the air supplied to the calorimeter and of the coal and solves the equations given above so as to accurately determine the heating value of the coal continuously and in real time.

The sulfur content is determined from the flue gases by an ultraviolet spectrometer, the temperature of which is monitored by TE711 and TE712. The transducer $AY_1$ which samples flue gas from the flue of the calorimeter 22 provides an output proportional to sulfur dioxide content of the flue gas and therefore of the coal. The precipitator and weighing means for ash measurement is not shown in FIG. 2.

Referring to FIG. 3, there is shown the electronic system for the calorimetry system shown in FIG. 2. There are the analog data board 47 with analog-to-digital converters for translating temperature and pressure analog signals into digital signals. The meter circuits #1–#6 convert other air and propane pressure and temperature signals and load cell force signals into digital signals. The microcomputer 12 uses the serial converter to read the meters digital signals (into the computer 12) via address codes which are carried on the data lines, which lines extend through the boards 45 and 47. Multiplexing therefore occurrs. Operation control for the system is inputted from a keyboard 43 and outputs to the motor controls and the igniter and also to the solenoid valves are provided from the digital data board 45 which also contains drive amplifiers to provide sufficient current for operating the switches and solenoids. It will be understood that there is a separate output from the digital data board to each solenoid valve and switch. The speed control signals for the motor controllers of the screw feeder FC901 and the belt feeder FC900 are supplied as variable frequency clock pulses from the computer 12 and alter the speed of the stepper motor 71 of the screw feeder 62. The computer operates in accordance with the program, the format and structure of which will be apparent from FIG. 11 to execute the various modes of operation of the calorimetry system and to compute the heating value, sulfur content and other measurements which are made during the operation of the system.

Figure 8:
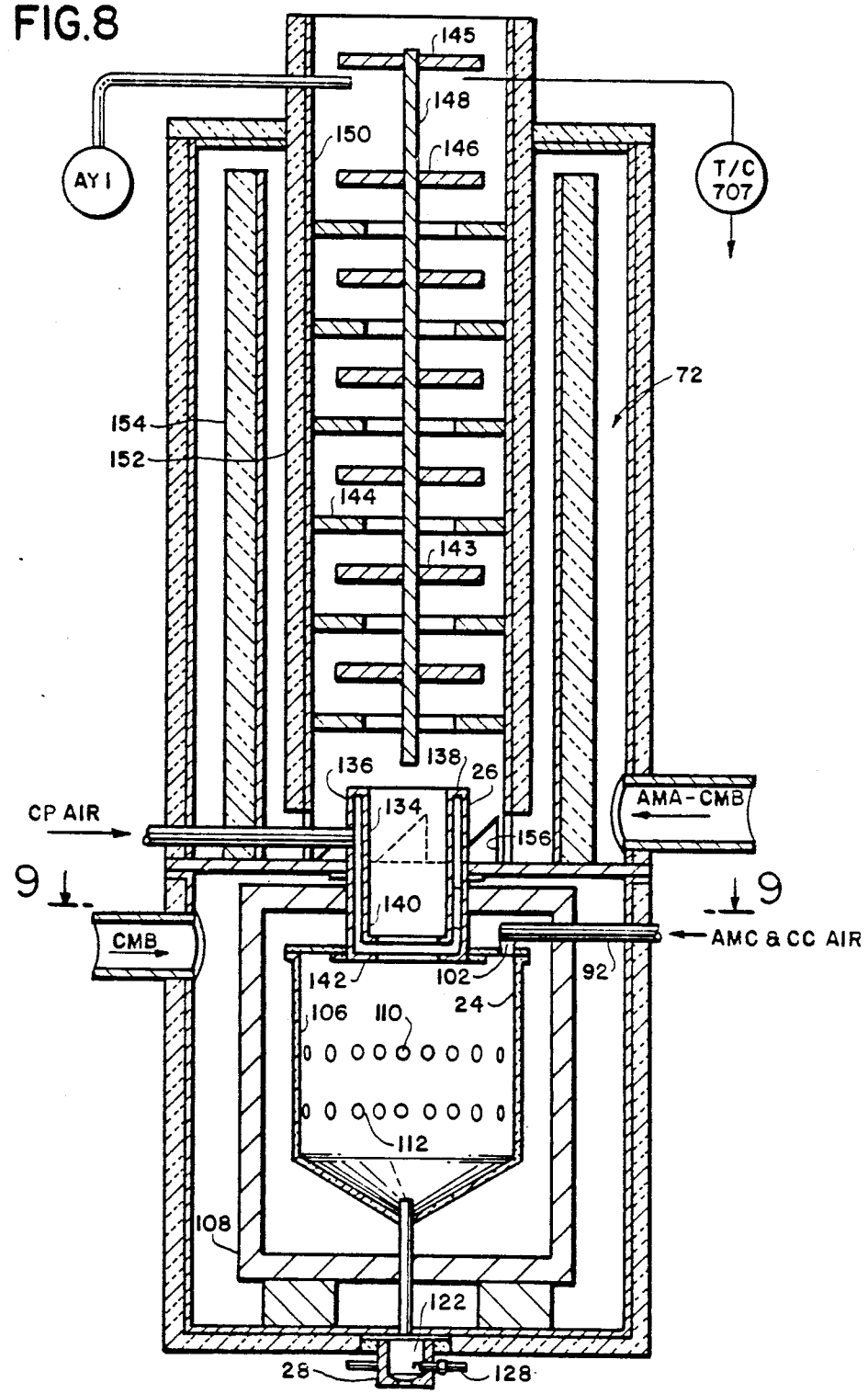
FIG. 8 is a diagrammatic view of the calorimeter shown in FIGS. 1 and 2.
Figure 9:
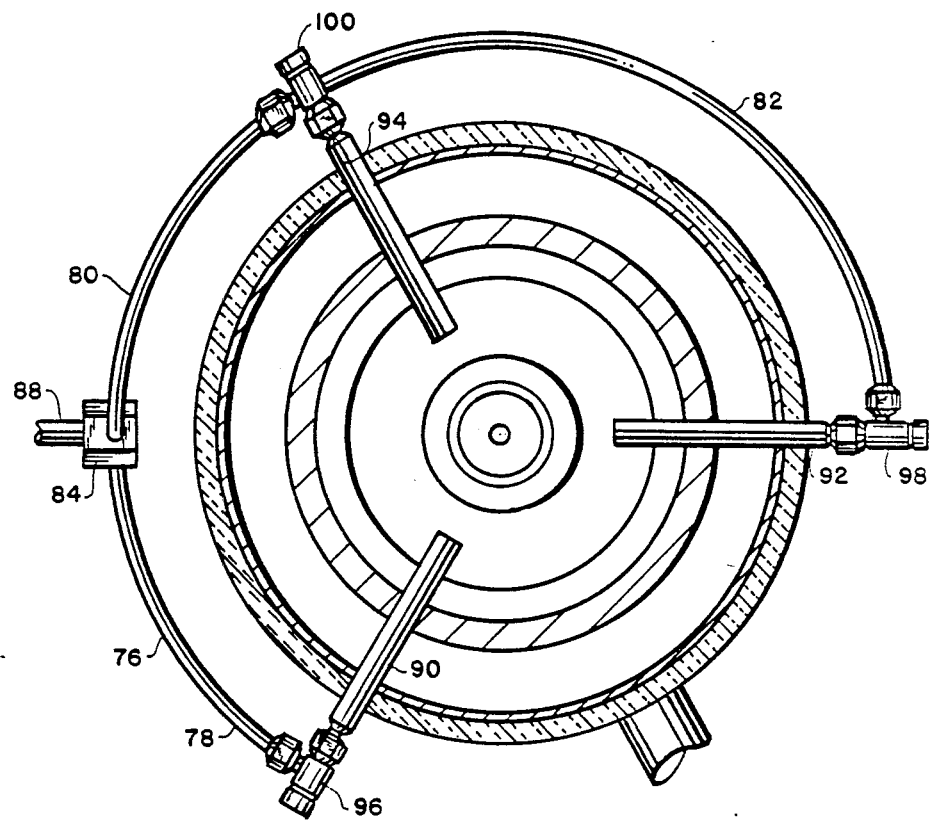
FIG. 9 is a sectional view of the calorimeter, the section being taken along the line 9—9 in FIG. 8.

Referring to FIGS. 8, 9, 10 and 10A, there is shown the calorimeter 22. It will be noted that in general, the design of the calorimeter 22 is similar to the calorimeter shown in the above-referenced United States patent application. The improvements in the calorimeter lie in the inclusion of the afterburner 26, the manifold piping for distributing the air and coal mixture into the combustor 24, which manifold arrangement is shown in FIG. 9, and in the igniter 28. The mixer, heat exchanger 30 has its center flue elongated so that the upper baffle disk 145 is above the heat recovery labyrinth 72.

The coal and air mixture amc and ccair enters the calorimeter 22 by being distributed with a manifold ring 76 having three arcuate pipes 78, 80 and 82 which are connected to a distributor coupling 84. The coupling is connected to the eductor 36 via a pipe 88. The manifold pipes are individually connected to three discharge pipes 90, 92 and 94. The pipes are easily cleaned of any clogs, since their couplings to the manifold pipe, the couplings being shown at 96, 98 and 100, can be disconnected and rods inserted to clear the pipes, if and when necessary. The ends of the discharge pipes are connected through nozzles, one of which 102 is shown in FIG. 8, into the top plate of the combustion chamber 106 of the combustor 24. There are similar nozzles connecting the two other discharge pipes, all of which are disposed at 120° separations from each other.

In the combustion chamber 106, the flow path of the coal is folded back on itself and the burning of the coal takes place in the centroid of the chamber 106. The circulation of the coal insures that it is fully burned without the collection of ash and all ash travels upwardly out of the combustor, through the mixer 30 and, finally, out of the calorimeter 22.

The secondary or combustion air cmb is provided by the blower 91 (FIG. 2). The combustion air is suitably 15 SCFM at 20 to 40 inches of water column as can be measured by the various pressure gauges and pressure transducers in the system. The secondary air gains access to the combustion chamber 106 by passing through a porous insulator cell 108 of ceramic material surrounding the chamber 106. The insulator is heated by radiative and conductive loss from the combustion chamber 106 and is cooled by the secondary air passing through it. During this passage, the secondary air is heated, picking up the radiated and conducted heat loss from the chamber 106 before entering the combustion chamber through two sets 110 and 112 of circumferentially spaced holes. Three additional holes (not shown) are disposed from approximately 120° apart in the cone-shaped bottom of the chamber 106 to assist in the circulation of the secondary air. In addition, there may be air holes spaced behind the nozzles 102 which extend downwardly from the distributor tubes 90, 92 and 94, all to improve the distribution and circulation of the air and coal mixture in the combustor chamber 106. The distributor tubes 90, 92 and 94 also carry the preheat propane and the calibrating propane during the preheat, standby and calibrate modes of operation of the system. The rows of circumferential holes 110 and 112 are disposed with their axes at 45° downwardly.

The igniter 28 consists of a hexagonal cylinder 120 having a combustion chamber bored therein. The combustion chamber 122 is sealed at the bottom by a plug 124. Tube 126 and another tube 127 approximately 120° behind the tube 126 provide inlets for high-pressure regulated air and propane into the chamber 122. Also entering the chamber 122 is an ignition device, namely a spark plug 128. As shown in FIG. 2, the spark plug BE20 is connected to the transformer (BY21). A flange 130 is provided for connection of the igniter 28 to the housing of the calorimeter 22. A tube 132 extends from the chamber 122 into the bottom of the combustion chamber 106. In operation, when a spark occurs in the chamber 122, a flame is generated which travels up the tube 132 into the combustion chamber where it ignites the propane and air mixture in the chamber to begin the preheat mode of operation of the system.

The afterburner 26 consists of inner and outer cylinders 134 and 136 which are closed by a ring 138 at the top of the afterburner. The air for the afterburner (cpair) comes from the cyclone. This air carries the moisture and the ultrafine coal into the annulus between the cylinders 134 and 136. This air circulates and is distributed around the annulus and flows into a region between two rings 140 and 142 at the bottom of the afterburner. There the coal is exposed to the flame rising upwardly from the combustor cell. In other words, the afterburner mixture of coal, moisture and air enters radially into the flame, the radial direction being defined by the rings 140 and 142 and the annulus between the cylinders 134 and 136. Accordingly, complete combustion of the ultrafine coal occurs so as to enhance the accuracy of the heating value computation. It is preferable to use the afterburner 26 rather than combining the cpair with the secondary air (amc+ccair), since the additional high-volume air flow of which the cpair consists could extinguish the flame in the combustor. It is also not desirable to combine the cpair with the combustion air cmb since the fines in the cpair could clog the porous cell 108.

The hot combustion products and cooling air mix by turbulent flow while traveling the length of the mixing and heat exchanger 30. Mixing is enhanced by the presence of baffles. These baffles are in the form of an alternating series of disks and rings 143 and 144 which increase the turbulence of the flow and the mixing. The temperature probe TE707 is located at the top of the calorimeter between uppermost disks 145 and 146. This disposition of the temperature probe isolates the probe at the exhaust outlet from the combustion chamber 106 and its flame to prevent temperature measurement errors due to radiant heating of the thermocouple. The disks 143, 145 and 146 are connected to a spine 148 which may be vibrated to further cause thermal agitation and mixing.

Heat losses to the mixing chamber are minimized by the labyrinthine pathway 72 for the cooling or mixing air ama-cmb. Heat passes from the mixture of combustion products and cooling air to the metal tubular wall 150 which defines the mixing chamber. This heat passage is by convection. Heat also passes to the layers of insulation 152 and 154 surrounding the mixing chamber. The cooling air flows along the surface of this insulation starting at the low temperature end and gains heat as it travels downwardly to the entrance openings 156. These entrance openings are triangular in shape to increase the turbulence as the cooling air enters the mixing chamber. The triangular flaps cut from the wall 150 to provide the openings 156 are bent backwardly to provide baffles internally of the mixing chamber to facilitate mixing and enhance turbulence. The cooling (or mixing) air thus improves the accuracy of the system since it picks up radiative, conductive and convective losses from the mixing chamber. The heating value computation is carried out using the temperature difference between the temperature of the cooling air $T_i$ and the $T_o$. Of course the enthalpy of all of the other materials flowing into the calorimeter are taken into account together with the temperature of the mixing air $T_i$ in determining the total temperature rise to $T_o$ at the outlet of the mixing chamber (the flue) at the top of the mixing chamber.

Figure 6:
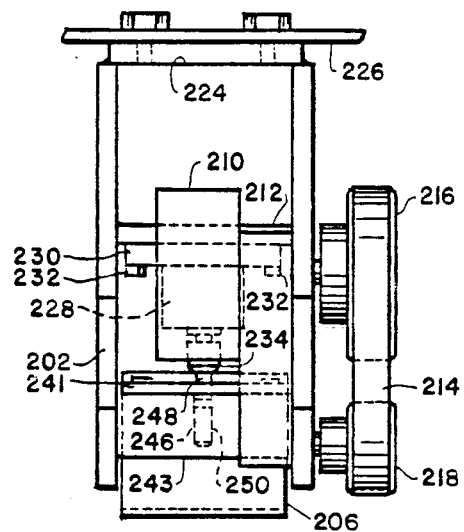
FIG. 6 is an end view from the left of the feeder shown in FIGS. 4 and 5.
Figure 7A:
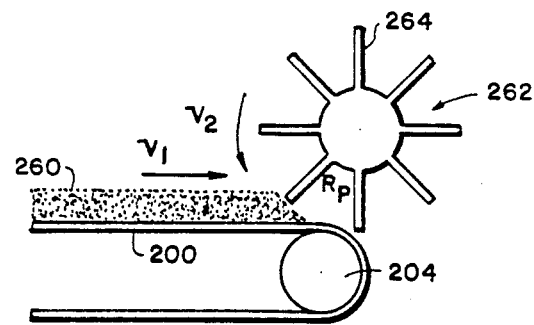
FIGS. 7 and 7A are diagrammatic views of the gravimetric belt feeder and the device for controlling the angle of repose (the angle of repose shaping device) at the head end pulley of the feeder.
Figure 7:
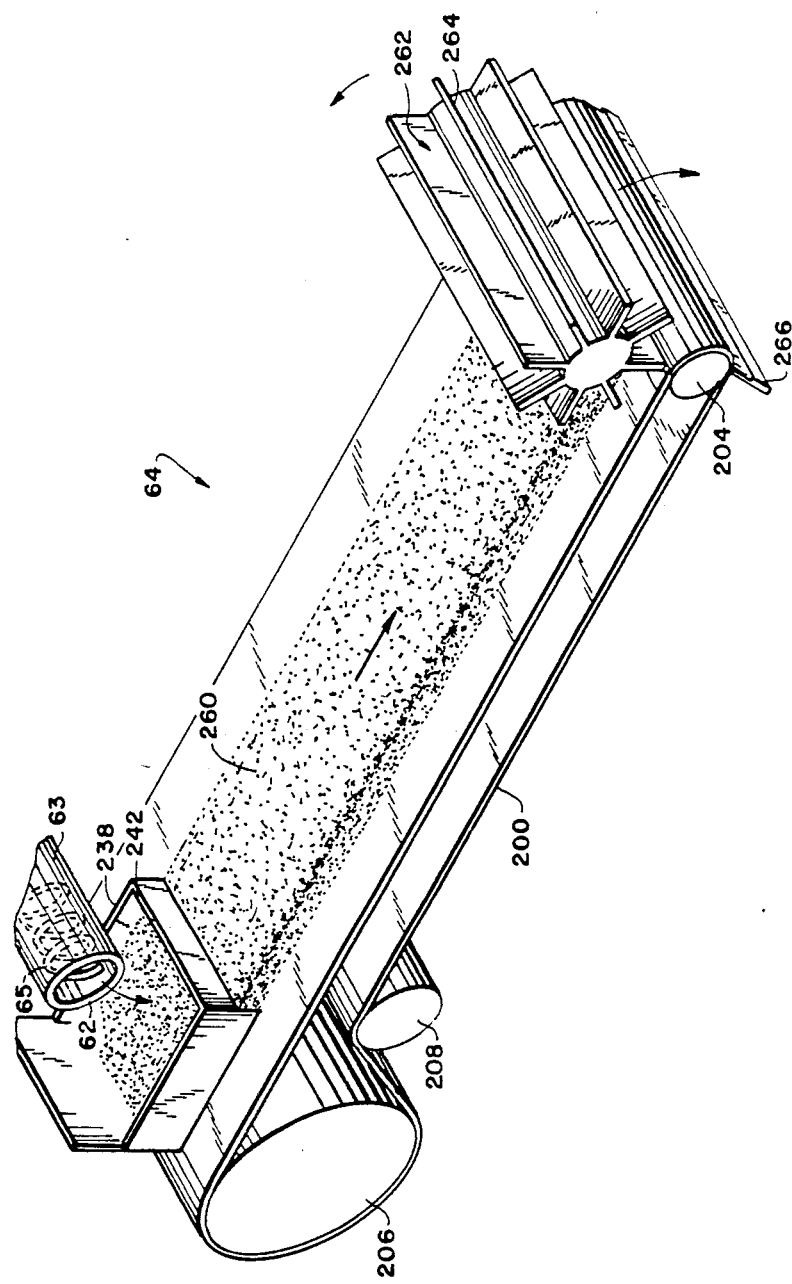

Referring more particularly to FIGS. 4 through 7 and also to FIG. 7A, the gravimetric belt feeder 64 will be shown together with the outlet end of the screw feeder 62.

The belt feeder has as its principal element a belt 200 which is of elastomeric material, preferably a fiber reinforced neoprene having a width extending between the sides of a support frame 202. The support frame has journalled therein a head end pulley 204 and a tail end pulley 206. These pulleys are shown diagrammatically in FIG. 2 at 66 and 68. It is a feature of this invention that the head end pulley is of minimal size and is significantly smaller than the tail end pulley which is necessarily large to provide the surface area necessary to drive the belt. To this end the belt is tightened and tensioned by a tensioning pulley 208.

One side 203 of the frame 202 extends rearwardly beyond the tail end pulley 206 and supports a drive motor 210 with its gear reducer 212. A cog belt 214 connects a motor pulley 216 and a pulley 218 which is connected to the tail pulley 206. For balancing and leveling purposes there is a screw 220 with a weight in the form of nuts 222 which may be adjustably positioned on the screw 220 and clamped against each other. The frame is supported as a lever on a bracket 224 which is attached to a support structure 226, a part of which is indicated in FIGS. 5 and 6. The support bracket is approximately the same width as the frame and carries a load cell 228 which is connected to a mounting plate 230 attached to the support bracket by screws 232. The load cell has an actuator button 234 which may be a composite of metal and elastomeric material for damping purposes.

The support bracket has a notch 233 through which the end of the screw feeder 62 extends over a guide 238 having side bars 240 and a leveling bar 242. The coal is deposited into this guide and is shaped by the guide into a generally rectangular strip on the top surface of the belt 200. The guide is attached to a bracket 241 which is connected to a bar 243 which extends across the frame under the button 234. Inside of this bar 243 there is a blind hole 246 which carries an overload pin 248 against which the load cell drive button 234 bears. The overload control is provided by a spring 250 which is captured in the hole 246 under the overload pin. The spring force developed by the spring 250 is higher than the load cell force rating but less than the overload limit of the load cell. Accordingly, the load cell is protected by the overload pin 248 and spring 250.

The location of the point of contact of the load cell to the overload pin is significant in order to provide high accuracy of measurement, since measurement accuracy is a function of the direction of the force as applied to the load cell. The force component equal to the force due to the weight of the coal on the belt (the moment) is directed into the load cell without any side forces or loads only when it is along the axis of the load cell. Any deviation from parallelism produces side loads on the cell which adversely affects its accuracy.

The fulcrum of the belt and frame assembly is provided by flexures 252 and 254 which are held against the support structure and frame, respectively, by screws 256. It is significant to the accuracy of weight measurement by belt feeder 64 that these flexures 252 and 254, which define the fulcrum of the lever, be at the vertical center of gravity of the assembly held by the frame 202. Since these pivot flexures and the fulcrum which they provide is located on or very close to the vertical center of gravity, the center of mass is neither above nor below the fulcrum. Therefore, the assembly does not exert a moment if it rotates, which might occur due to an accidental displacement of the lever or a change in level of the support structure 226. This avoids pendulum effects. Also the parts which define the fulcrum (i.e. the flexures 252, 254 and the load cell support 226) are preferably of material having the same coefficient of thermal expansion to avoid forces which might produce load cell measurement errors.

In obtaining a horizontal balance, the counterweights 222 are adjusted to provide a positive force against the drive button 234, thereby preloading the cell 228 and thus avoiding errors from operating tonear the zero load condition of the load cell. The point of contact between the pin 248 and the drive button 234 is along a radial line to the fulcrum defined by the flexures 252 and 254. Accordingly, the axis of the load cell will be perpendicular to the radial from the fulcrum and side loads on the load cell are avoided, thereby improving its measurement accuracy.

More specifically, in the feeder there is a first plane which passes through the load cell axis and the point of contact of the pin 248 and button 234. This first plane is tangent to the radial line (the radius) to the fulcrum. The fulcrum is the center of rotation of the assembly. A second plane passes through the point of contact and the fulcrum. The first and second planes are perpendicular to each other. A horizontal plane will pass through the vertical center of gravity and the fulcrum which are close to or coincident.

The load cell measures the reaction due to the weight of the coal on the belt 200. This reaction is determined principally by the length of the body of coal on the belt 200. This body of coal is shown diagrammatically at 260 in FIGS. 7 and 7A. The coal, due to the moisture therein and its relatively small particle size, has the tendency to cling to the belt as the belt 200 travels around the head pulley 204. This has the tendency to form a momntary cantilever of indeterminate length at the end of the body of coal. It is an important feature of the invention that the length of the body of coal 260 be precisely controlled so that the coal has a fixed angle of repose indicated as the angle $R_p$ between a vertical line to the center of the head pulley 204 and the leading edge of the coal body 260.

This angle of repose is obtained in two ways. First, the head pulley 204 is of minimum diameter which reduces the surface on which the coal can bear as it slides off the belt. Another contributing element is an angle of repose control device or shaper 262 which is disposed above the head pulley 204 and has vanes 264 which engage the leading edge of the body of coal 260. The shaper is driven at a speed higher than the speed of the belt so as to sweep the coal off the belt so that it drops into the feed funnel 84 (FIG. 2). Accordingly, the weigh span and resulting moment of the coal body is limited and made definite regardless of the cohesiveness of the coal. The angle of repose of the coal on the belt at the delivery point is controlled and accuracy of weighing is improved. While the vanes are shown as fins, they may also be a row of pins and the term "vane" shall be deemed to include such pin structures.

A scraper 266 is mounted opposite to the shaper 262 to clean the belt for the next rotation. In order to drive the shaper, a pair of gears may be used, the larger gear which is coupled to the shaft of the head pulley is shown at 268 in FIG. 4. Its cooperating gear on the shaft of the shaper 262 is not shown to simplify the illustration. It may be desirable to provide a helical twist to the vanes of the shaper 262 to provide a more continuous flow of coal off the belt into the feed funnel 84. The vanes may be provided by a row of pins which extends radially from the axis of the distributor along a helical path from one end of the shaper to the other. This arrangement also provides a more uniform flow of the coal and provides less surface for adherence of the coal.

The screw feeder 62 is shown as a tube 63 having an auger made up of a helical wire 65 rotatable therein. A separate motor 71 (FIG. 2) is used to drive the auger at a variable rate. By reducing the rate of auger feed, the width of the body 260 of coal may be adjusted for mass feed rate control in the system.

The computer determines the mass feed rate of the coal from the product of the radius of the head pulley and its rpm multiplied by 2 pi/60, so as to obtain the rate of movement of the body 260 along the belt in distance units per second. This quantity is multiplied by the distance ($l_f$) between the load cell contact point and the fulcrum and also by the force detected at the load cell. The entire quantity is divided by the length ($l_s$) of the body of coal on the belt. Expressed mathematically, the formula is $m = W_r/l_s^2 (ksl_fnr)$ where m is the mass feed rate of the coal, $W_r$ is the force in grams measured by the load cell, $l_s$ is the length of the body 260 of coal on the belt, r is the radius of the head pulley, s is the speed of the motor in rpm, and n is the ratio of the gears and the pulleys (the speed reduction ratio) between the motor and the tail pulley, k is a constant to change the units into mass speed rate in terms of grams per second.

It will be appreciated that the output of the load cell is a current which is a function of the weight in grams. This current is converted by the analog digital convertor in the meter #6 device (FIG. 3) into a digital signal for the computer. Since the motor speed is controlled by the $f_s$ control signal, the computer has in its memory the motor speed. The other constants are stored in the memory of the computer so that the mass speed rate computation can be obtained. The program will be more evident from the flow charts in FIG. 11.

Figure 11A:
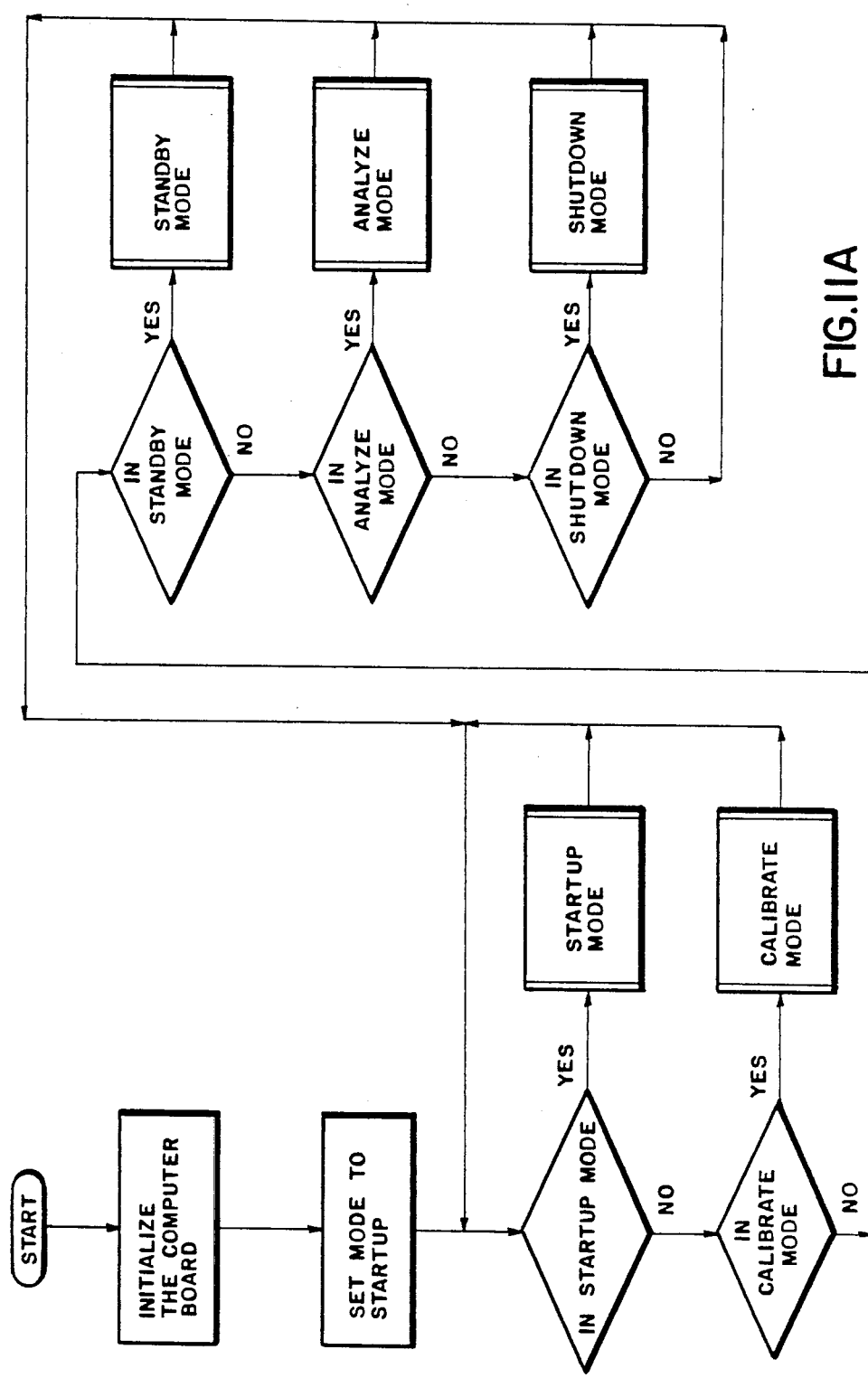
Figure 11B:
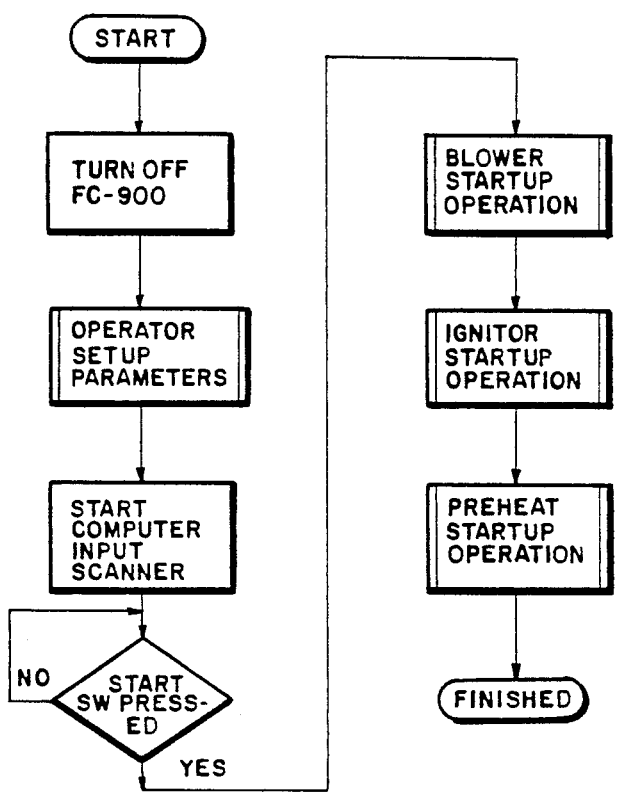
Figure 11J:
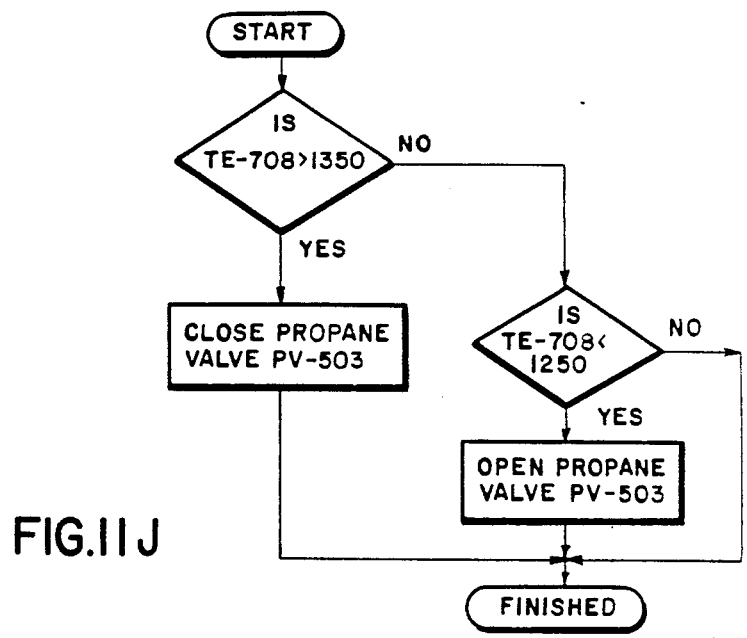
Figure 11D:
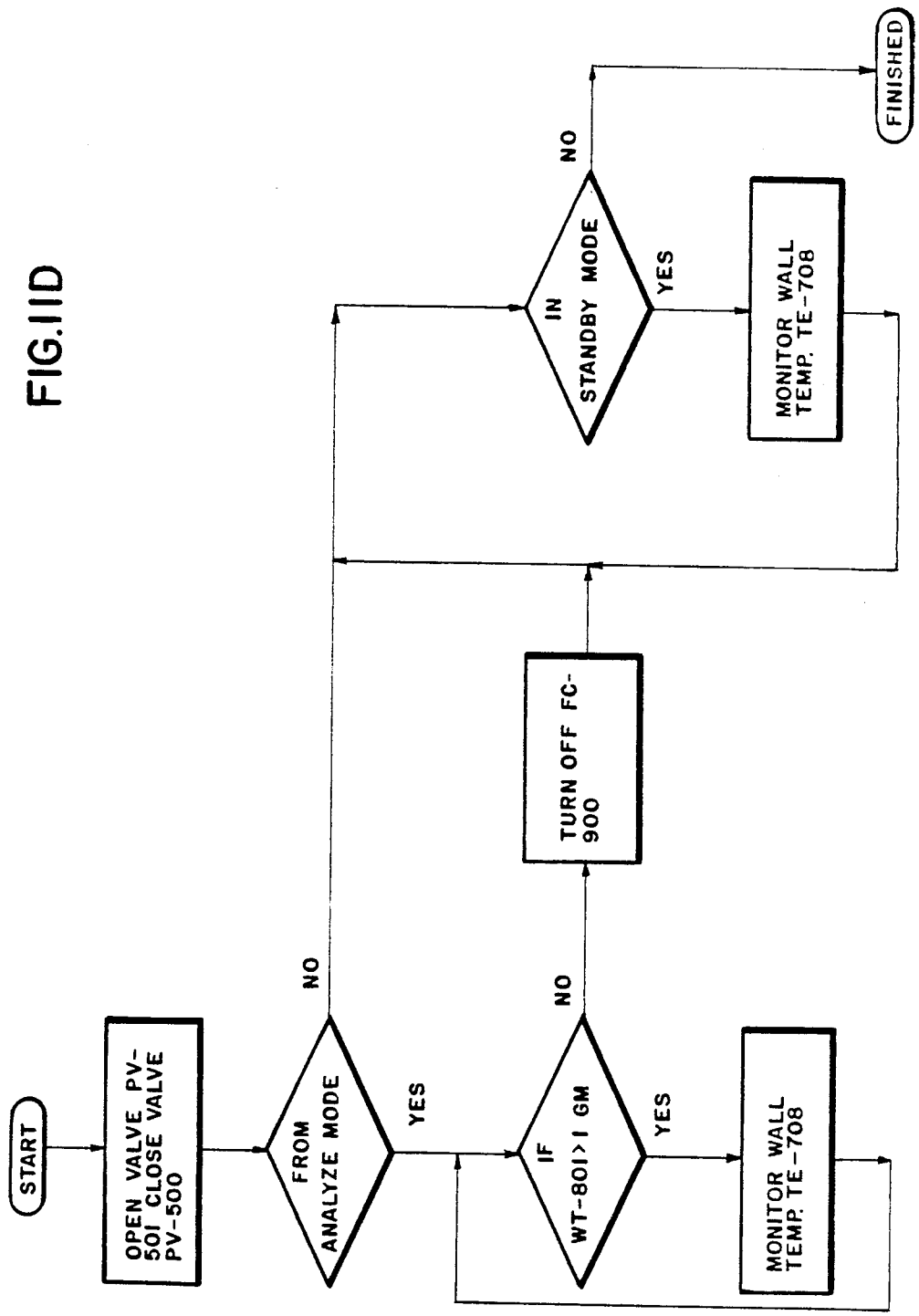
Figure 11E:
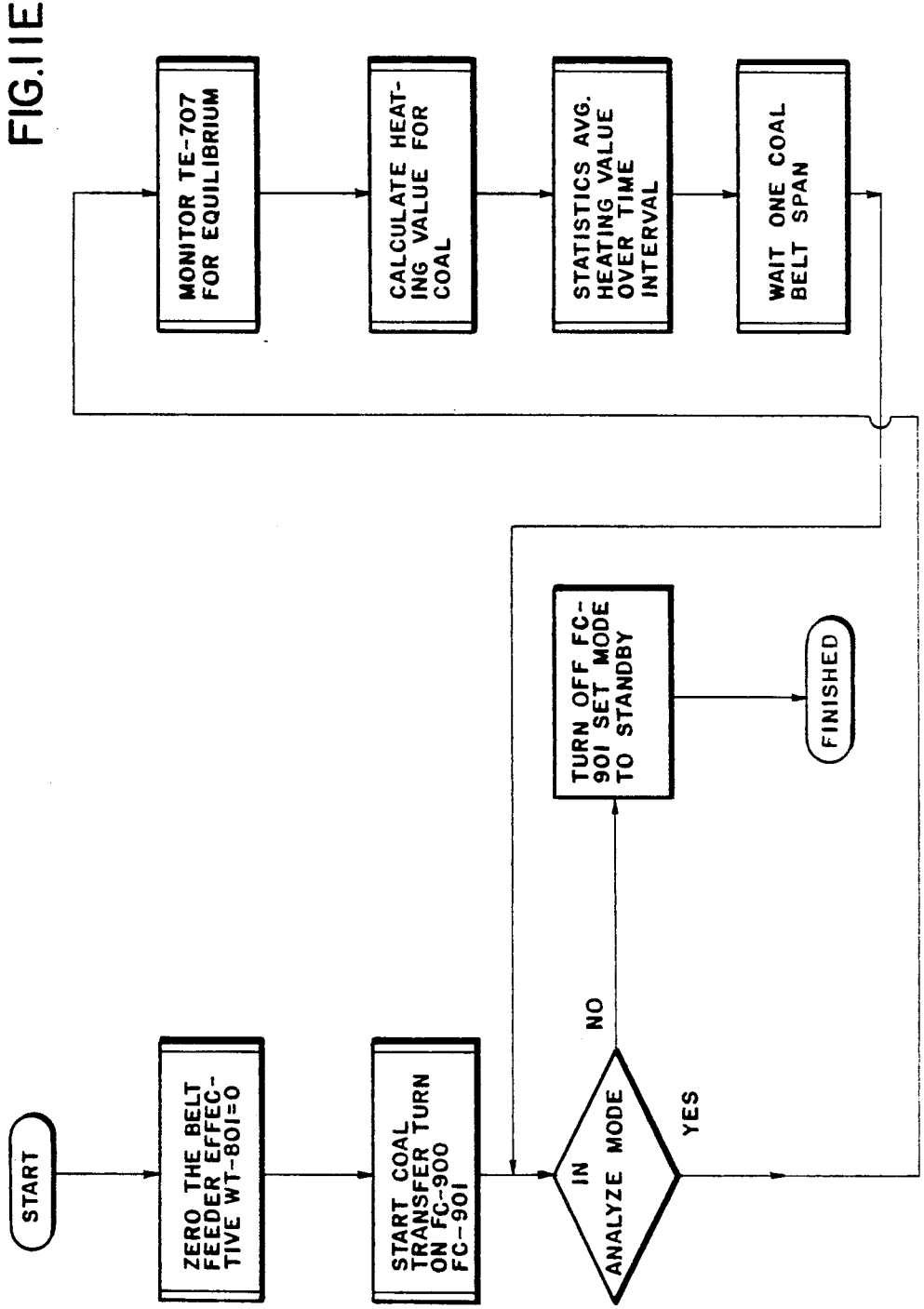
Figure 11F:
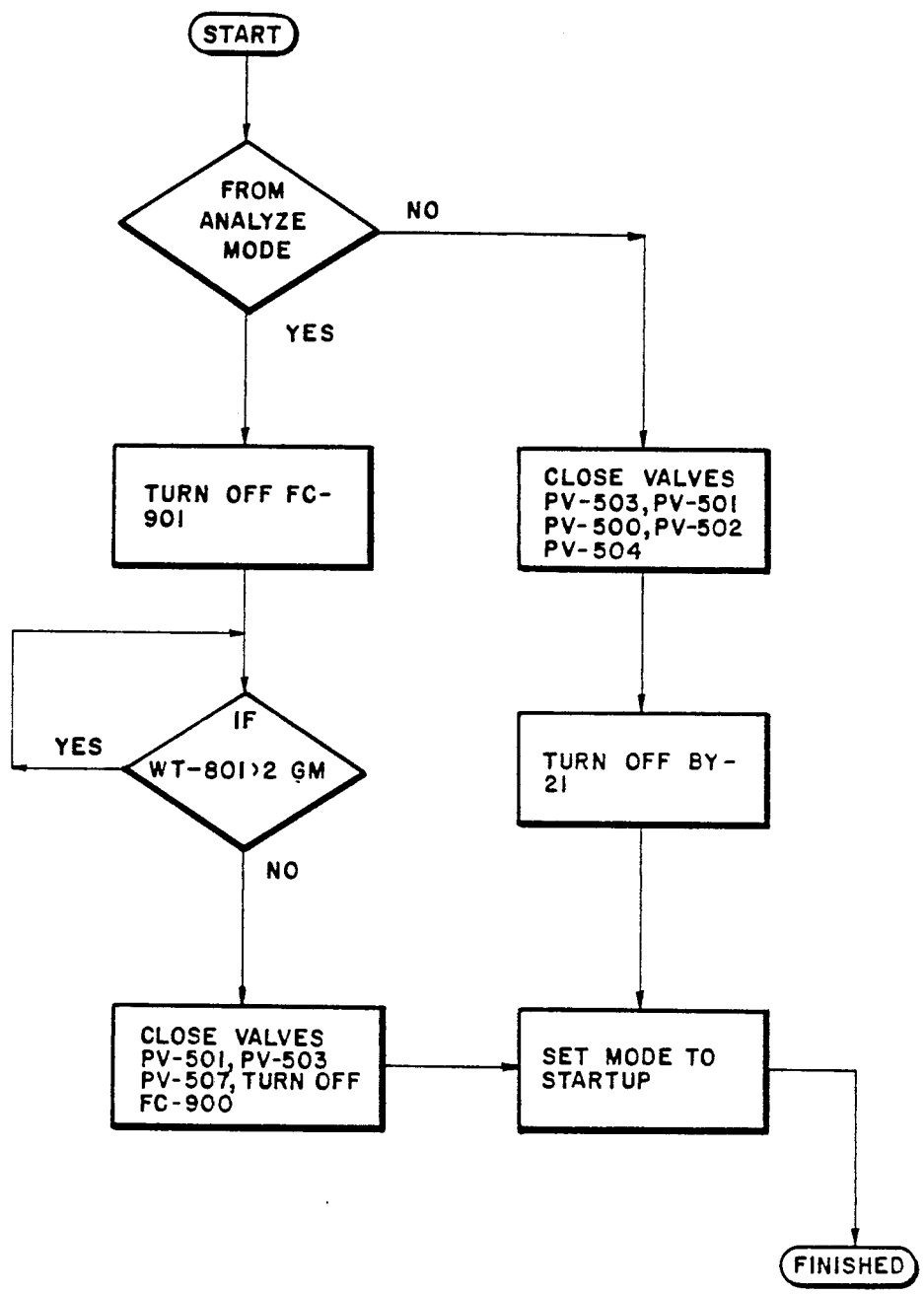
Figure 11G:
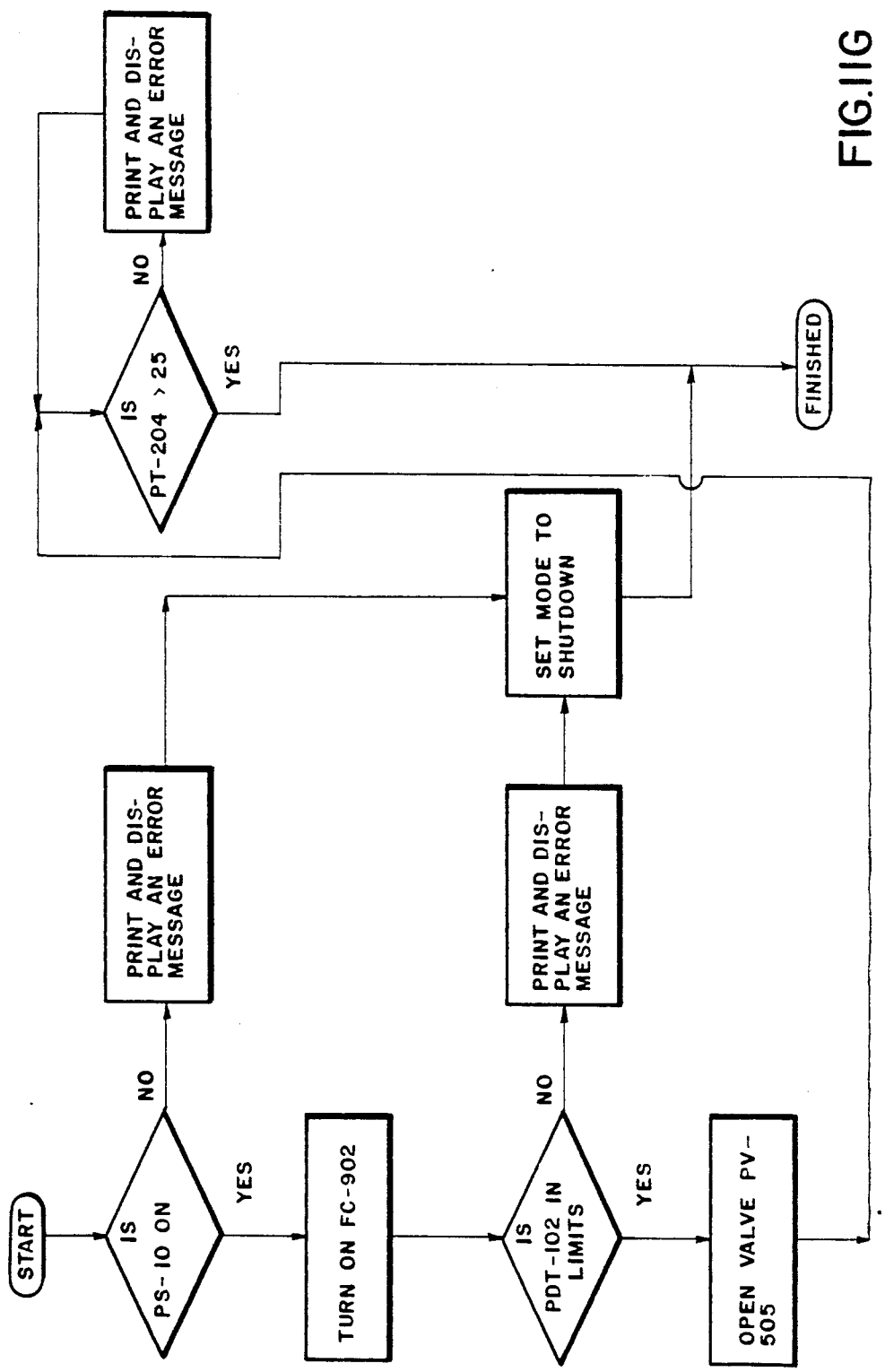
Figure 11:
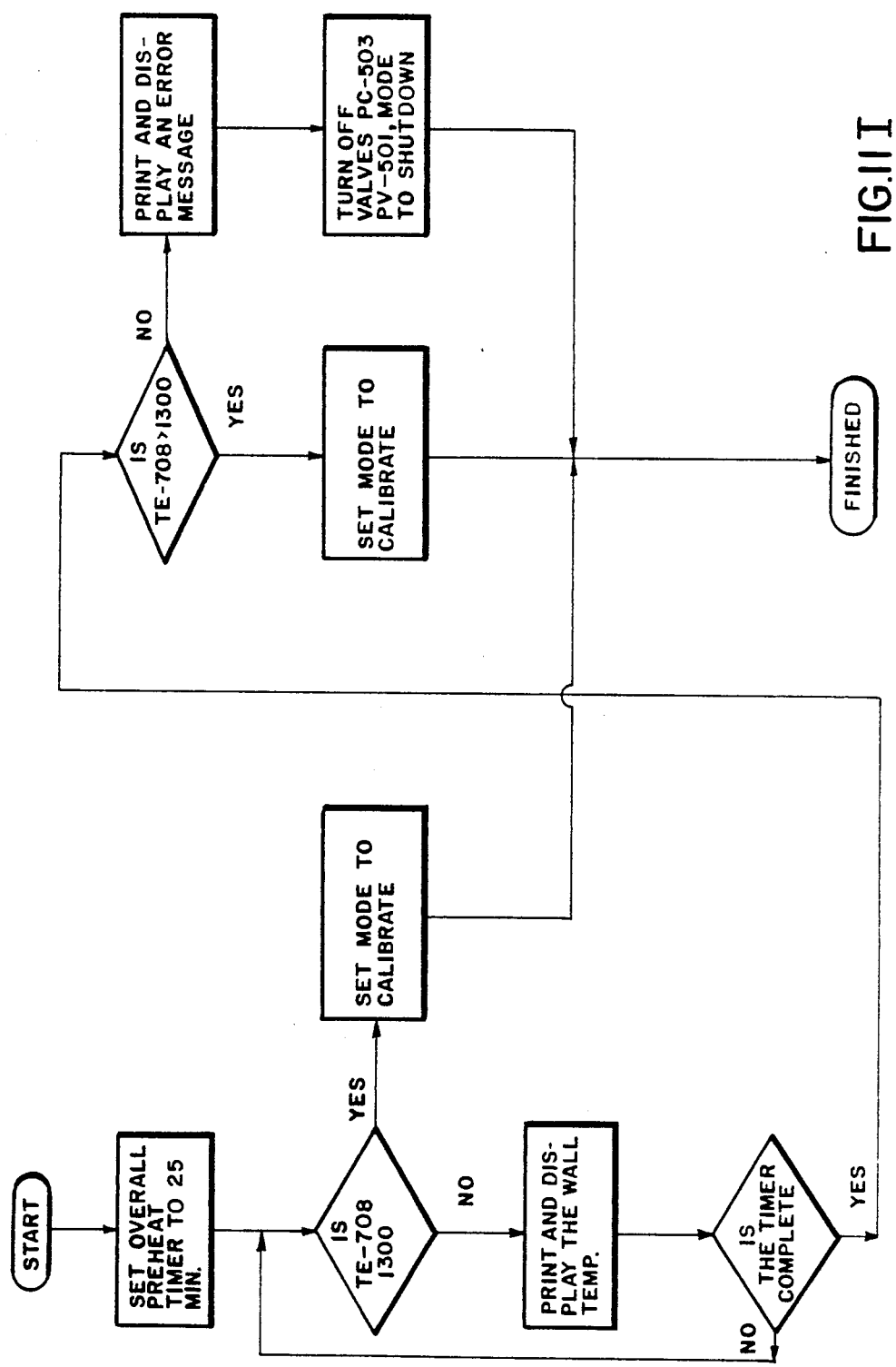

The structure and format of the computer programs which are executed by the computer 12 will be apparent from FIG. 11. FIG. 11A shows in general the complete program with the program processes for the initialization of the system as well as the start-up, calibrate, standby, analyze and shutdown modes which were discussed above.

FIG. 11B shows the start-up mode program. It will be noted that the computer is executing one of its modes at all times after power up and initialization. At the completion of the start-up mode, the calorimeter will be at operating temperature and automatically goes into calibration. The calibration mode program is shown in FIG. 11C. After calibration, the system automatically goes into standby. The standby program is illustrated in FIG. 11D. It will be apparent from the flow chart of FIG. 11D that, depending upon operator selection (while the program is waiting for operator input from the keyboard), the system stays in standby mode.

From standby mode the analyze or calibrate mode can be entered. The analyze mode program is shown in FIG. 11E.

From the analyze program the operator can return to standby or shut down the system. The shut down program is illustrated in FIG. 11F. After shut down the system is prepared to enter the start up mode again when the operator selects that mode.

FIGS. 11G, H and I respectively show the submodules of the start up mode program of FIG. 11B. Namely, FIG. 11G shows the blower start up program for the low pressure air blower 91 (FIG. 2). FIG. 11H shows the program for starting the igniter 28. FIG. 11I shows the preheat Program which is used during the start up mode.

It is desirable to monitor the wall temperature continuously during the standby mode thereby protecting the combustor. The program for this monitoring operation is shown in FIG. 11J.

From the foregoing description, it will be apparent that there has been provided an improved calorimetry system which is capable of determining, to a higher degree of accuracy than heretofore practicable, the heating value of coal and other solid fuels in real time and directly, together with the sulphur content and, if desired, the ash content of the fuel. Variations and modifications of the herein described system, within the scope of the invention, will undoubtedly suggest themselves to those skilled in the art. Accordingly, the foregoing description should be taken as illustrative and not in a limiting sense.

We claim:

1. In a calorimetry system for the direct and continuous measurement of the heating value of solid fuel material, such as coal, by the combustion thereof in a combustor to produce combustion gas which is mixed with a mixing gas in a mixer and the measurement of the temperatures of the gases and the mass flow rates of the material, the improvement which comprises means for processing the material prior to combustion into a first stream of air which contains said material essentially of particles, and a second stream of air containing the moisture in said material and particles of said material finer than the particles in said first stream, an after burner preceding said mixer and in the output stream of said combustor, and means for feeding said first stream into said combustor and said second stream into said after burner.

2. The improvement according to claim 1 further comprising means for measuring the mass feed rate of said material preceding said processing means.

3. The improvement according to claim 2 wherein said mass feed measurement means comprises an endless belt disposed around tail and head pulleys which are spaced from each other and at least one of which is rotated to move said belt, means defining a fulcrum on which said belt is pivotally mounted, means for forming said material into a moving body on said belt, said body having a length extending along one side of said belt, means for measuring the force due to the weight of said body, and means engageable with said body for maintaining said length at a certain length.

4. The improvement according to claim 3 wherein said length maintaining means comprises means for providing a certain angle of repose of said body on said belt as said body and belt rotates around said head pulley.

5. The improvement according to claim 3 wherein said length maintaining means comprises said head pulley, wherein said head pulley is much smaller in diameter than said tail pulley.

6. The improvement according to claim 5 wherein said head pulley radius is the minimum bend radius of said belt which is approximately equal to the inside radius of said belt when folded over upon itself.

7. The improvement according to claim 4 wherein said angle of repose providing means comprises a member rotatably mounted opposite to said head pulley, said member having a peripheral portion engageable with the end of said body adjacent to said head pulley.

8. The improvement according to claim 7 wherein said body has a vane or vanes extending radially thereof and circumferentially spaced from each other for engaging and shaping the end of said body which terminates adjacent to said head pulley.

9. The improvement according to claim 7 further comprising means for rotating said member such that the peripheral speed of said engageable portion is greater than the surface speed of said belt.

10. The improvement according to claim 3 further comprising a frame on which said pulleys and belt are mounted, a support, means connecting said frame to said support to define said fulcrum, a load cell mounted on said support and engageable with a portion of said frame as it pivots to provide for the measurement of said force, said load cell, said support and said frame connecting means, having essentially the same coefficient of thermal expansion.

11. The improvement according to claim 3 further comprising a frame on which said pulley and belt are mounted, a support, means connecting said frame to said support to define said fulcrum with said frame extending with said belt in one direction away from said fulcrum and said frame also extending in a direction opposite to said one direction away from said fulcrum, and a load cell mounted on said support and engageable with the portion of said frame spaced in said opposite direction from said fulcrum.

12. The improvement according to claim 11 wherein said load cell has an actuating member extending therefrom and moveable along an axis, a contactor member extending from said portion of said frame into engagement with said actuating member, and means yieldably biasing said contactor member against said actuating member to preload said cell.

13. The improvement according to claim 12 wherein a plane extending radially through said fulcrum is perpendicular to said axis.

14. The improvement according to claim 13 wherein said contactor is mounted in said portion for reciprocating movement along an axis aligned with the axis along which said actuator is moveable when said frame and the components mounted thereon and pivotal therewith, including said belt, is horizontal and balanced about said fulcrum.

15. The improvement according to claim 10 wherein said frame has side members disposed along opposite sides of said belt, said fulcrum providing means comprising flexures connecting said opposite sides to said support.

16. The improvement according to claim 12 wherein said actuating member has a button at the end thereof which engages said contactor, said button having a body of elastomeric damping material disposed therein.

17. The improvement according to claim 3 wherein said force measuring means includes a member moveable along an axis, said axis being perpendicular to a plane extending radially to said fulcrum which pivots about said fulcrum with said belt.

18. The improvement according to claim 17 wherein said force measuring means is a load cell having said member extending therefrom, said member having an end surface, a frame carrying said belt and being pivotally mounted on said fulcrum, a contactor mounted on said frame and pivotable therewith about a radius centered at said fulcrum, said contactor having an end in contact with the end of said member extending from said load cell, said frame and the components assembled thereon having a vertical center of gravity, and said fulcrum being disposed close to or coincident with each other.

19. The improvement according to claim 1 wherein said processing means comprises a fluid energy driven mill for pulverizing said material when driven by pressurized air to provide a stream of air carrying pulverized material at an outlet thereof, a cyclone separator having an inlet in communication with said outlet, said cyclone having first and second outlets from which said first and second streams are emitted, said first outlet being in communication with said combustor and said second outlet being in communication with said after burner.

20. The improvement according to claim 19 wherein said combustor comprises a chamber with ends and sides, an opening into one of said ends, said after burner having inner and outer tubes aligned with said opening in said combustor, said tubes being spaced from each other to define an annulus extending away from said one end of said chamber, said annulus being closed at the end thereof away from said chamber and open at the end thereof at said one end of said chamber, and said second outlet being in communication with said after burner via a pipe extending into said annulus.

21. The improvement in accordance with claim 20 wherein rings are provided in the ends of said tubes which define radial extensions of said annulus toward the center of said end wall opening of said chamber.

22. The improvement according to claim 19 wherein said combustor comprises a chamber having end and side walls, an opening in an end wall communicating with said mixer via said after burner.

23. The improvement in accordance with claim 22 further comprising a plurality of pipes extending radially toward said after burner and disposed above said end wall, nozzles extending from said pipes through said end wall into said chamber, manifold pipes connecting said radially extending pipes to said first outlet via detachable fittings at the ends of said radially extending pipes opposite to said nozzles, said fitting being detachable for the insertion of clean outrods into said radial pipes.

24. The improvement according to claim 22 further comprising an igniter having an ignition chamber, a pipe extending from said ignition chamber into said combustion chamber, means for supplying air and fuel gas to said ignition chamber, and means for igniting said air and fuel gas in said ignition chamber.

25. The improvement according to claim 24 wherein said ignition means is a spark plug extending into said ignition chamber.

26. The improvement according to claim 22 wherein said combustor chamber is disposed within a cell of porous refractory material, a plurality of rows of openings extending around the side wall of said chamber, and means for supplying secondary air to said chamber through said porous cell.

27. The improvement according to claim 22 wherein said mixer comprises a tube around said after burner, said tube having opposite ends one end being disposed around said after burner and the end opposite thereto being spaced away from said after burner, an opening in said tube adjacent to the end around said after burner for admission of mixing air.

28. The improvement according to claim 22 wherein said mixer comprises a plurality of tubes, a center one of which provides a mixing chamber and is in communication with said after burner, others of said plurality of tubes defining concentric annuluses around said mixing chamber connected to define passages for the flow of said mixing air in opposite directions towards and away from a mixing air admission opening, said mixing air admission opening being disposed in said inner tube and adjacent to said after burner.

29. The improvement according to claim 22 wherein said mixer has a mixing chamber which extends from said combustor to an end thereof away from said combustor, means in said mixing chamber near the end thereof which is spaced away from said combustor for measuring the temperature of the combustion gases and air mixed in said mixing chamber, means also disposed near the end of said mixing chamber away from said combustor for extracting gas therefrom for the measurement of constituents of said gas selected from the group consisting of sulphur dioxide and ash.

30. The improvement according to claim 1 wherein said processing means controls the feeding of said material and feeds all of said material including said first and second streams into said combustor or afterburner.

* * * * *